US010967058B2

(12) United States Patent
Dominowski et al.

(10) Patent No.: US 10,967,058 B2
(45) Date of Patent: *Apr. 6, 2021

(54) FOOT-AND-MOUTH DISEASE VACCINE

(71) Applicants: Zoetis Services LLC, Parsippany, NJ (US); United States of America, as Represented by the Secretary of Agriculture, Washington, DC (US)

(72) Inventors: Paul Joseph Dominowski, Kalamazoo, MI (US); John Morgan Hardham, Kalamazoo, MI (US); James Alan Jackson, Kalamazoo, MI (US); Cyril Gerard Gay, Bethesda, MD (US); Luis Leandro Rodriguez, Niantic, CT (US); Peter William Krug, East Setauket, NY (US); Aida Elizabeth Rieder, Westbrook, CT (US)

(73) Assignees: Zoetis Services LLC, Parsippany, NJ (US); United States of America, as represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/374,105

(22) Filed: Apr. 3, 2019

(65) Prior Publication Data

US 2020/0078456 A1  Mar. 12, 2020

Related U.S. Application Data

(63) Continuation of application No. 15/543,630, filed as application No. PCT/US2016/013587 on Jan. 15, 2016, now Pat. No. 10,478,487.

(60) Provisional application No. 62/104,314, filed on Jan. 16, 2015.

(51) Int. Cl.
| | |
|---|---|
| *A61K 39/135* | (2006.01) |
| *A61K 39/12* | (2006.01) |
| *A61K 39/39* | (2006.01) |
| *A61K 39/00* | (2006.01) |

(52) U.S. Cl.
CPC ............ *A61K 39/135* (2013.01); *A61K 39/12* (2013.01); *A61K 39/39* (2013.01); *A61K 2039/5252* (2013.01); *A61K 2039/552* (2013.01); *A61K 2039/555* (2013.01); *A61K 2039/55505* (2013.01); *A61K 2039/55511* (2013.01); *A61K 2039/55561* (2013.01); *A61K 2039/55566* (2013.01); *A61K 2039/55583* (2013.01); *C12N 2770/32034* (2013.01); *C12N 2770/32134* (2013.01)

(58) Field of Classification Search
None
See application file for complete search history.

(56) References Cited

U.S. PATENT DOCUMENTS

| | | | |
|---|---|---|---|
| 4,471,054 A | 9/1984 | Lattore et al. | |
| 4,732,971 A | 3/1988 | DiMarchi | |
| 10,117,921 B2* | 11/2018 | Dominowski | ... G01N 33/56944 |
| 10,478,487 B2* | 11/2019 | Dominowski | ....... A61K 39/135 |
| 2005/0118701 A1* | 6/2005 | Zhou | ..................... A61K 31/395 435/239 |
| 2008/0038295 A1* | 2/2008 | Baker, Jr. | ............. A61K 39/285 424/232.1 |
| 2009/0324641 A1* | 12/2009 | Dominowski | ........ A61K 39/215 424/207.1 |
| 2011/0014232 A1* | 1/2011 | Maree | .................. C07K 14/005 424/216.1 |
| 2011/0129494 A1* | 6/2011 | Detraz | .................... A61K 39/00 424/204.1 |
| 2012/0315295 A1* | 12/2012 | Rieder | ................. A61K 39/135 424/205.1 |
| 2020/0078456 A1* | 3/2020 | Dominowski | ......... A61K 39/39 |

OTHER PUBLICATIONS

Instant SEQ ID No. 8 alignment with Geneseq access No. ARW70773 by Debelak et al. in WO 2008068638 Jun. 2008.*
Stills Jr. (ILAR Journal; 2005; 46(3): 280-293).*
Ren et al. (Vaccine. 201; 29: 7960-7965).*
Valarcher, J.-F., et al., "Incursions of Foot-and-Mouth Disease Virus into Europe between 1985 and 2006," Journal Compilation © 2008 Blackwell Verlag • Transboundary and Emerging Diseases. 55 (2008), pp. 14-34.
Perez, Andres M., et al., "Variation in the VP1 gene of Foot-and-mouth disease virus serotype A associated with epidemiological characteristics of outbreaks in the 2001 epizootic in Argentina," J. Vet. Diagn. Invest. 20: pp. 433-439 (2008).
Perez, Andres M., et al., "Control of a foot-and-mouth disease epidemic in Argentina," Preventive Veterinary Medicine 65 (2004) pp. 217-226.
Stram, Yehuda, et al., "Nucleotide Sequence of the PI Region of Serotype Asia I Foot-and-Mouth Disease Virus," Virus Genes 8:3, pp. 275-278, 1994.
Carrillo, C., et al., "Comparative Genomics of Foot-and-Mouth Disease Virus†," Journal of Virology, May 2005, pp. 6487-6504.
Pereda, A.J., et al., "Full length nucleotide sequence of foot-and-mouth disease virus strain O1 Campos/Bra/58," Arch Virol (2002) 147: pp. 2225-2230.

* cited by examiner

*Primary Examiner* — Shanon A. Foley
(74) *Attorney, Agent, or Firm* — Vyacheslav Vasilyev

(57) ABSTRACT

Compositions for prevention of Foot and Mouth Disease (FMD) are provided, comprising an antigen component in the amount equivalent to 0.5-20 µg FMD virus and an adjuvant component comprising oil, an immunostimulatory oligonucleotide, and a polycationic carrier. Methods of using the composition, as well as the methods of reducing FMD persistence are also provided.

19 Claims, 1 Drawing Sheet
Specification includes a Sequence Listing.

| | | | | | | | | | | |
|---|---|---|---|---|---|---|---|---|---|---|
| Marker | Pre-10 micron filter pellet | Pre-10 micron filter sup | Post-10 micron filter | Post-4.5 micron filter | Post-.8/.2 micron filter | One hour post-BEI w/ thio | Vaccine Batch #3 | BEI/Vacc Peg Fract #10 | A24 Control | A24 Control (1:10) |

← anti FMDV-3D Mab F19-59

← anti FMDV-VP1 Mab 6HC4

1　2　3　4　5　6　7　8　9　10　11

FOOT-AND-MOUTH DISEASE VACCINE

CROSS REFERENCE TO RELATED APPLICATIONS

This Application is a continuation of U.S. application Ser. No. 15/543,630 filed on Jul. 14, 2017, now allowed, which is the National Stage of International Application No. PCT/US2016/013587, filed on Jan. 15, 2016, which application claims the benefit of U.S. Provisional Application No. 62/104,314, filed Jan. 16, 2015.

THE NAMES OF THE PARTIES TO A JOINT RESEARCH AGREEMENT

The claimed invention was made as a result of activities undertaken within the scope of a joint research agreement between Zoetis LLC and the United States Department of Agriculture, Agricultural Research Service.

BACKGROUND

Foot and mouth disease (FMD) is an extremely contagious viral disease of cloven-hoofed ungulates which include domestic animals (cattle, pigs, sheep, goats, and others) and a variety of wild animals. The most prominent disease symptoms in FMDV-infected cattle include vesicular lesions of the epithelium of the mouth, tongue, teats and feet. Although some countries, among them United States, Canada, Mexico, Australia and most of Europe, are considered to be free of FMD, the disease is distributed worldwide and has a great economic impact on the export industry. Indeed, several economically devastating outbreaks have occurred over the past decade on almost every continent.

Currently killed-antigen FMDV vaccines are necessarily produced in expensive biological containment facilities, by growing large volumes (thousands of liters) of virulent FMDV that has been adapted to grow in cells, which can be sometimes difficult. This process has resulted in escape of virulent virus from the manufacturing facility causing costly outbreaks in livestock (see Cottam et al. 2008. PLoS Pathogen 4:1-8). After growth, virus is then inactivated using chemicals and antigen concentrates are prepared, followed by purification steps required to remove contaminant proteins. It is difficult to differentiate infected from vaccinated animals (DIVA) through serological diagnostic tests. There is little to no cross protection across serotypes and subtypes requiring the appropriate matching between vaccine and circulating field strains to achieve protection. Despite these shortcomings of the vaccines, billions of doses are manufactured every year around the world. Their use has been the basis for eradicating FMDV from Europe and for controlling the disease in many parts of the world through mass vaccination campaigns. Creation of genetically engineered viruses containing a backbone and suitable restriction sites partially addresses the shortcomings of inactivated vaccines as restriction sites provide loci for introduction of capsid proteins of different FMD strains. Nevertheless, the cost of antigen is the greatest contributor to the cost of FMD and most other vaccines.

The problem of FMD control is further exacerbated by the phenomenon of virus persistence. Briefly, historically, inactivated FMD vaccines have been unable to prevent persistence or carrier state (defined as virus shedding past 28 days following infection and/or exposure). Shedding animals, while not exhibiting any FMD symptoms, could remain a source of FMD infection to other animals. As such, commonly accepted disease control practices require slaughter of all animals in a vaccinated herd even if they do not have clinical signs of disease.

As such, methods and compositions which lead to vaccines with a lower antigen load without compromising efficiency and/or reducing or eliminating FMD persistence are still desired.

SUMMARY OF THE INVENTION

In one aspect, the invention provides an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide, and at least one of a polycationic polymer; a source of aluminum; and the antigen component comprises a FMD antigen composition in the amount equivalent to 0.5-8 µg of FMD virus per dose.

In certain embodiments, the immunostimulatory oligonucleotide is a CpG containing oligonucleotide. In certain embodiments, the polycationic polymer is DEAE dextran.

In different embodiments, the antigen is an FMD virus composition, and is present in the amount of 0.5-4 µg per dose, or 0.5-2 µg per dose, or 0.5-1 µg per dose, or in the amount of about 0.5 µg per dose.

The FMD virus may be inactivated or attenuated. In certain embodiments, the FMD virus is an inactivated FMD A24 Cruzeiro strain. In selected embodiments, the inactivated strain is a genetically engineered strain which contains a deletion of the leader coding region (LL) and optionally, contains negative antigenic markers.

In certain embodiments, the genetically engineered virus contains capsid proteins from a heterologous strain.

In another aspect, the invention provides a method of preventing FMD in an animal in need thereof, the method comprising administering the immunogenic composition according to the embodiments of the previous aspect to said animal. In different embodiments, the animal is selected from bovines, ovines, porcines, and caprines.

In another aspect, the invention provides a method of reducing frequency of FMD persistence in a ruminant infected with FMD comprising administering to said ruminant prior to the infection an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose.

In yet another aspect, the invention provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are not slaughtered.

The invention also provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are quarantined for 0-62 days.

The invention also provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are moved beyond the infected zone.

BRIEF DESCRIPTION OF THE DRAWINGS

FIG. 1 illustrates the difference in quality between the PEG precipitated and hollow fiber concentrated antigens.

DETAILED DESCRIPTION

Definitions

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater, unless about is used in reference to time intervals in weeks where "about 3 weeks," is 17 to 25 days, and about 2 to about 4 weeks is 10 to 40 days.

"Adjuvant" means any substance that increases the humoral or cellular immune response to an antigen. Adjuvants are generally used to accomplish two objectives: the controlled release of antigens from the injection site, and the stimulation of the immune system.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to any substance that is recognized by the animal's immune system and generates an immune response. The term includes killed, inactivated, attenuated, or modified live bacteria, viruses, or parasites. The term "antigen" also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"Buffer" means a chemical system that prevents change in the concentration of another chemical substance, e.g., proton donor and acceptor systems serve as buffers preventing marked changes in hydrogen ion concentration (pH). A further example of a buffer is a solution containing a mixture of a weak acid and its salt (conjugate base) or a weak base and its salt (conjugate acid).

"Consisting essentially" as applied to the adjuvant formulations refers to formulation which does not contain unrecited additional adjuvanting or immunomodulating agents in the amounts at which said agent exert measurable adjuvanting or immunomodulating effects.

"Dose" refers to a vaccine or immunogenic composition given to a subject. A "first dose" or "priming vaccine" refers to the dose of such a composition given on Day 0. A "second dose" or a "third dose" or an "annual dose" refers to an amount of such composition given subsequent to the first dose, which may or may not be the same vaccine or immunogenic composition as the first dose.

The term "emulsifier" is used broadly in the instant disclosure. It includes substances generally accepted as emulsifiers, e.g., different products of TWEEN® or SPAN® product lines (fatty acid esters of polyethoxylated sorbitol and fatty-acid-substituted sorbitan surfactants, respectively), and different solubility enhancers such as PEG-40 Castor Oil or another PEGylated hydrogenated oil.

"Humoral immune response" refers to one that is mediated by antibodies.

"Immune response" in a subject refers to the development of a humoral immune response, a cellular immune response, or a humoral and a cellular immune response to an antigen. Immune responses can usually be determined using standard immunoassays and neutralization assays, which are known in the art.

"Immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

"Immunogenic" means evoking an immune or antigenic response. Thus an immunogenic composition would be any composition that induces an immune response.

"Infected Premises" refers to premises where presumptive positive case or confirmed positive case exists based on laboratory results, compatible clinical signs, FMD case definition, and international standards.

"Infected Zone" refers to an area within 3 km beyond perimeters of presumptive or confirmed Infected Premises.

"Lipids" refers to any of a group of organic compounds, including the fats, oils, waxes, sterols, and triglycerides that are insoluble in water but soluble in nonpolar organic solvents, are oily to the touch, and together with carbohydrates and proteins constitute the principal structural material of living cells.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"$TCID_{50}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, Virology Methods Manual, p. 25-46 (1996).

Persistently infected or carrier animals are animals shedding FMD virus past 28 days post infection or onset of clinical disease.

Adjuvant Formulations and Methods of Making

The instant application discloses several adjuvant formulations suitable for the instant invention. The common feature of these adjuvants is the presence of oil and one or more emulsifiers, wherein the oily phase comprises at least 50% of the vaccine composition encompassing the adjuvant formulations disclosed therein.

Multiple oils and combinations thereof are suitable for use of the instant invention. These oils include, without limitations, animal oils, vegetable oils, as well as non-metabolizable oils. Non-limiting examples of vegetable oils suitable in the instant invention are corn oil, peanut oil, soybean oil, coconut oil, and olive oil. A non-limiting example of an animal oil is squalane. Suitable non-limiting examples of non-metabolizable oils include light mineral oil, straight chained or branched saturated oils, and the like.

In a set of embodiments, the oil used in the adjuvant formulations of the instant invention is a light mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.) or USB Corporation (Cleveland, Ohio). Preferred mineral oil is light mineral oil commercially available under the name DRAKEOL®.

In certain embodiments particularly suitable for preventing or eliminating FMD persistence, the oily phase is present in an amount from 50% to 95% by volume; preferably, in an amount of greater than 50% to 85%; more preferably, in an amount from greater than 50% to 60%, and more preferably in the amount of greater than 50-52% v/v of the vaccine composition. The oily phase includes oil and emulsifiers (e.g., SPAN® 80, TWEEN® 80, etc.), if any such emulsifiers are present. The volume of the oily phase is calculated as a sum of volumes of the oil and the emulsifier(s). Thus, for example, if the volume of the oil is 40% and the volume of the emulsifier(s) is 12% of a composition, then the oily phase would be present at 52% v/v of the composition. Similarly, if the oil is present in the amount of about 45% and the emulsifier(s) is present in the amount of about 6% of a composition, then the oily phase is present at about 51% v/v of the composition.

It also should be understood that since the adjuvants of the instant invention form only a part of the vaccines of the instant invention, the oily phase is present in an amount from 50% to 95% by volume; preferably, in an amount of greater than 50% to 85%; more preferably, in an amount from 50% to 60%, and more preferably in the amount of 50-52% v/v of each of the adjuvants of the instant invention.

In a subset of embodiments, the volume percentage of the oil and the oil-soluble emulsifier together is at least 50%, e.g., 50% to 95% by volume; preferably, in an amount of greater than 50% to 85%; more preferably, in an amount from 50% to 60%, and more preferably in the amount of 50-52% v/v of the vaccine composition. Thus, for example and without limitations, the oil may be present in the amount of 45% and the lipid-soluble emulsifier would be present in the amount of greater than 5% v/v. Thus, the volume percentage of the oil and the oil-soluble emulsifier together would be at least 50%.

In yet another subset, applicable to all vaccines of the invention, volume percentage of the oil is over 40%, e.g., 40% to 90% by volume; 40% to 85%; 43% to 60%, 44-50% v/v of the vaccine composition.

Emulsifiers suitable for use in the present emulsions include natural biologically compatible emulsifiers and non-natural synthetic surfactants. Biologically compatible emulsifiers include phospholipid compounds or a mixture of phospholipids. Preferred phospholipids are phosphatidylcholines (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, and phosphatidylethanolamine. The phospholipids may be isolated from natural sources or conventionally synthesized.

In additional embodiments, the emulsifiers used herein do not include lecithin, or use lecithin in an amount which is not immunologically effective.

Non-natural, synthetic emulsifiers suitable for use in the adjuvant formulations of the present invention include sorbitan-based non-ionic surfactants, e.g. fatty-acid-substituted sorbitan surfactants (commercially available under the name SPAN® or) ARLACEL®, fatty acid esters of polyethoxylated sorbitol)(TWEEN®, polyethylene glycol esters of fatty acids from sources such as castor oil)(EMULFOR®; polyethoxylated fatty acid (e.g., stearic acid available under the name SIMULSOL® M-53), polyethoxylated isooctylphenol/fornnaldehyde polymer)(TYLOXAPOL®, polyoxyethylene fatty alcohol ethers) (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and SPAN®-80 (sorbitan monooleate).

Generally speaking, the emulsifier(s) may be present in the vaccine composition in an amount of 0.01% to 40% by volume, preferably, 0.1% to 15%, more preferably 2% to 10%.

Additional ingredients present in the instant adjuvant formulations include cationic carriers, immunostimulatory oligonucleotides, monophospholipid A and analogs thereof (MPL-A), Polyinosinic:polycytidylic acid (poly I:C), saponins, quaternary ammoniums, sterols, glycolipids, a source of aluminum (e.g., REHYDRAGEL® or VAC 20° wet gel) and combinations thereof.

Suitable cationic carriers include, without limitations, dextran, dextran DEAE (and derivatives thereof), PEGs, guar gums, chitosan derivatives, polycellulose derivatives like hydroxyethyl cellulose (HEC) polyethylenimene, poly aminos like polylysine and the like.

Suitable immunostimulatory oligonucleotides include ODN (DNA-based), ORN (RNA-based) oligonucleotides, or chimeric ODN-ORN structures, which may have modified backbone including, without limitations, phosphorothioate modifications, halogenations, alkylation (e.g., ethyl- or methyl-modifications), and phosphodiester modifications. In some embodiments, poly inosinic-cytidylic acid or derivative thereof (poly I:C) may be used.

CpG oligonucleotides are a recently described class of pharmacotherapeutic agents that are characterized by the presence of an unmethylated CG dinucleotide in specific base-sequence contexts (CpG motif). (Hansel T T, Barnes Pi (eds): New Drugs for Asthma, Allergy and COPD. Prog Respir Res. Basel, Karger, 2001, vol 31, pp 229-232, which is incorporated herein by reference). These CpG motifs are not seen in eukaryotic DNA, in which CG dinucleotides are suppressed and, when present, usually methylated, but are present in bacterial DNA to which they confer immunostimulatory properties.

In selected embodiments, the adjuvants of the instant invention utilize a so-called P-class immunostimulatory oligonucleotide, more preferably, modified P-class immunostimulatory oligonucleotides, even more preferably, E-modified P-class oligonucleotides. P-class immunostimulatory oligonucleotides are CpG oligonucleotides characterized by the presence of palindromes, generally 6-20 nucleotides long. The P-Class oligonucleotides have the ability to spontaneously self-assemble into concatamers either in vitro and/or in vivo. These oligonucleotides are, in a strict sense, single-stranded, but the presence of palindromes allows for formation of concatamers or possibly stem-and-loop structures. The overall length of P-class immunostimulatory oligonucleotides is between 19 and 100 nucleotides, e.g., 19-30 nucleotides, 30-40 nucleotides, 40-50 nucleotides, 50-60 nucleotides, 60-70 nucleotides, 70-80 nucleotides, 80-90 nucleotides, 90-100 nucleotides.

In one aspect of the invention the immunostimulatory oligonucleotide contains a 5' TLR activation domain and at least two palindromic regions, one palindromic region being a 5' palindromic region of at least 6 nucleotides in length and connected to a 3' palindromic region of at least 8 nucleotides in length either directly or through a spacer.

The P-class immunostimulatory oligonucleotides may be modified according to techniques known in the art. For example, J-modification refers to iodo-modified nucleotides. E-modification refers to ethyl-modified nucleotide(s). Thus, E-modified P-class immunostimulatory oligonucleotides are P-class immunostimulatory oligonucleotides, wherein at least one nucleotide (preferably 5' nucleotide) is ethylated. Additional modifications include attachment of 6-nitro-benzimidazol, O-methylation, modification with proynyl-dU, inosine modification, 2-bromovinyl attachment (preferably to uridine).

The P-class immunostimulatory oligonucleotides may also contain a modified internucleotide linkage including, without limitations, phosphodiester linkages and phosphorothioate linkages. The oligonucleotides of the instant invention may be synthesized or obtained from commercial sources.

P-Class oligonucleotides and modified P-class oligonucleotides are further disclosed in published PCT application no. WO2008/068638, published on Jun. 12, 2008. Suitable non-limiting examples of modified P-class immunostiumulatory oligonucleotides are provided below ("*" refers to a phosphorothioate bond and "-" refers to a phosphodiester bond).

SEQ ID NO: 1
5' T*C-G*T*C-G*A*C-G*A*T*C-G*G*C*G*C-G*C*G*C*G 3'

SEQ ID NO: 2
5' T*C-G*A*C*G*T*C*G*A*T*C*G*G*C*G*C*G*C*C*G 3'

SEQ ID NO: 3
5' T*C*G*A*C*G*T*C*G*A*T*C*G*G*C*G*C*G*C*G*C*C*G*T 3'

SEQ ID NO: 4
5' JU*C-G*A*C*G*T*C*G*A*T*C*G*G*C*G*C*G*C*G*C*G 3'

SEQ ID NO: 5
5' JU*C-G*A*C*G*T*C*G*A*T*C*G*G*C*G*C*G*C*G*C*C*G*T 3'

SEQ ID NO: 6
5' JU*C*G*A*C*G*T*C*G*A*T*C*G*G*C*G*C*G*C*G*C*C*G*T 3'

SEQ ID NO: 7
5' EU*C-G*A*C*G*T*C*G*A*T*C*G*G*C*G*C*G*C*G*C*G 3'

SEQ ID NO: 8
5' JU*C-G*T*C*G*A*C*G*A*T*C*G*G*C*G*G*C*C*G*C*C*G*T 3'

SEQ ID NO: 9
5' JU*C*G*T*C*G*A*C*G*A*T*C*G*G*C*G*G*G*C*C*G*C*C*G*T 3'

SEQ ID NO: 10
5' T*C-G*T*C-G*A*C-G*A*T*C-G*G*C*G*C-G*C*G*C*G 3'

SEQ ID NO: 11
5'-UUGUUGUUGUUGUUGUUGUU-3'

SEQ ID NO: 12
5'-UUAUUAUUAUUAUUAUUAUU-3'

SEQ ID NO: 13
5'-AAACGCUCAGCCAAAGCAG-3'

SEQ ID NO: 14
dTdCdGdTdCdGdTdTdTdTrGrUrUrGrUrGrUdTdTdT-3'

The amount of P-class immunostimulatory oligonucleotide for use in the adjuvant compositions depends upon the nature of the P-class immunostimulatory oligonucleotide used and the intended species.

In addition to the oil and the emulsifier(s), the adjuvant formulations also comprise (or consist essentially of, or consist of) a combination of an immunostimulatory oligonucleotide and a polycationic carrier. These adjuvants are referred to as "TXO".

In a set of embodiments, the TXO adjuvants may also include a source of aluminum, such as $Al(OH)_3$ gel. The TXO adjuvants with aluminum are referred to as "TXO-A".

In a set of embodiments, adjuvants TXO and TXO-A may optionally contain a sterol, such as, for example, cholesterol, lanosterol, sigmasterol, etc. TXO and TXO-A adjuvants containing the sterol are referred to as TCXO and TCXO-A, respectively. The optionally present sterol may be present in the amount of up to about 1000 µg (e.g., 100-1000 µg, 200-1000 µg, 250-700 µg, or about 400-500 µg) per dose.

In a set of embodiments, in TXO adjuvants, the immunostimulatory oligonucleotide, preferably an ODN, preferably containing a palindromic sequence, and optionally with a modified backbone, may be present in the amount of 5-400 µg per dose, and the polycationic carrier may be present in the amount of 5-400 mg per dose.

For example, in certain embodiments, one dose of TXO would comprise between about 5 and 400 µg per dose (e.g., 6.25-200 µg or 6.25-100 µg or 6.25-50 µg or 6.25-25 µg or 6.25-10 µg or 10-200 µg or 25-200 µg or 25-100 µg or 25-50 µg or 25-100 µg or 50-100 µg per dose) of the immunostimulatory oligonucleotide, and the polycationic carrier may be present in the amount of between about 5 and about 500 mg per dose (e.g., 6.25-200 mg or 6.25-100 mg or 6.25-50 mg or 6.25-25 mg or 6.25-10 mg or 10-200 mg or 25-200 mg or 25-100 mg or 25-50 mg or 25-100 mg or 50-100 mg per dose).

In certain embodiments, TXO adjuvants are prepared as follows:
a) Sorbitan monooleate is dissolved in light mineral oil. The resulting oil solution is sterile filtered;
b) The immunostimulatory oligonucleotide, Dextran DEAE and Polyoxyethylene (20) sorbitan monooleate are dissolved in aqueous phase, thus forming the aqueous solution; and
c) The aqueous solution is added to the oil solution under continuous homogenization thus forming the adjuvant formulation TXO.

In a set of embodiments, in TXO-A adjuvants, the immunostimulatory oligonucleotide is present as in the TXO adjuvant, the source of aluminum is present in the amount of up to 40% v/v (e.g., 35%, 30%, 25%, 20%, 15%, 10%, 5%, 1%). In a set of embodiments, the source of aluminum is present at 2%-20% v/v of the vaccine composition, more preferably between about 5% and about 17% v/v.

In certain embodiments, TXO-A adjuvants are prepared similarly to TXO adjuvants, and the source of aluminum is added to the aqueous solution.

In preparation of TCXO and TCXO-A adjuvants, cholesterol is dissolved in the oil solution, and the other steps of making TCXO and TCXO-A are similar to the steps used in preparation of TXO and TXO-A, respectively.

Antigens

The inventors have surprisingly discovered that the adjuvants of the instant invention are capable of causing sufficient protection from Foot-And-Mouth disease even when the dose of the antigen is decreased from 10 µg of the FMD virus to 0.5 µg. Thus, in different embodiments of the invention, the amount of the FMD virus may be 0.5 µg, about 1 µg, about 2 µg, about 3 µg, about 4 µg, about 5 µg, about 6 µg, about 7 µg, about 8 µg, about 9 µg or about 10 µg. The amount of the antigen may be between 0.5 and 1 µg, between 1 and 2 µg, between 2 and 3 µg, between 3 and 4 µg, between 4 and 5 µg, between 5 and 6 µg, between 6 and 8 µg, between 8 and 10 µg of FMD virus (140 S particles).

Currently, seven serotypes of FMD have been isolated. Of the seven serotypes of this virus, A, C, O, Asia 1, and SAT3 appear to be distinct lineages; SAT 1 and SAT 2 are unresolved clades. Within each serovar, multiple strains exist. For example, A24 Cruzeiro belongs to serotype A, and O1 Campos belongs to serotype O.

FMD virus of any serotype may be used as an antigen in this invention, provided that such virus is not pathogenic. Pathogenicity may be reduced by inactivation of the virus, e.g., treatment with formaldehyde or BEI.

In certain embodiments, the virus may be attenuated by culture passage or via recombinant means. It has previously been demonstrated, for example, that deletion of the leader protein $L^{pro}$ coding region results in FMD virus which is attenuated in cattle and pigs. See, e.g., U.S. Pat. Nos. 5,824,316, 8,765,141, Virology 1997 227(1): 96-102, J. Virol 2012 86:11675-11685. Point mutations in at positions 55 and 58 within the SAP domain of L protein also resulted in a viable virus that displayed a mild attenuated phenotype in cell culture and was protective in swine FMD model. See U.S. Pat. No. 8,846,057.

In certain embodiments, the virus also contains negative antigenic markers which allow for DIVA (differentiating infected from vaccinated animals) assays. In certain embodiments, the negative antigenic markers are introduced to 3D and/or 3B proteins. See, e.g., SEQ ID NOs 19, 20, 21, 22.

Like other viruses, the FMD virus continually evolves and mutates, thus one of the difficulties in vaccinating against it is the huge variation between, and even within, serotypes. There is no cross-protection between serotypes (a vaccine for one serotype will not necessarily protect against any others) and in addition, two strains within a given serotype may have nucleotide sequences that differ by as much as 30% for a given gene. This means FMD vaccines must be highly specific to the strain involved.

Thus, in certain embodiments, endonuclease restriction sites are introduced into the genome of the virus, thereby allowing introduction of proteins (e.g., proteins forming the outer capsids) from heterologous FMD strains.

In certain embodiments, the antigen component comprises FMD strain A24 Cruzeiro, which may optionally be modified by deletion of leader protein, negative marker mutations in 3B and/or 3D proteins, and by introduction of restriction endonuclease sites for an easier introduction of sequences for antigens (e.g., capsid proteins) from heterologous strains. Suitable non-limiting examples of the antigens are described in U.S. Pat. No. 8,765,141. DNA sequences corresponding to RNA genome of a genetically modified FMDV are also provided in SEQ ID NO: 15 ($A_{24}LL3D_{YR}$) and SEQ ID NO: 17 ($A_{24}LL3B_{PVKV}3D_{YR}$). Thus, a DNA sequence complementary to the DNA sequence set forth e.g., in SEQ ID NO: 15 is a template for, i.e. is complementary to or "encodes", the RNA genome of the FMDV virus (i.e., RNA that encodes the FMDV). In certain embodiments, the virus comprises capsid protein(s) of heterologous FMD strains (i.e., strains of FMD other than A24 Cruzeiro, including without limitations, strains of lineages C, O, Asia 1, SAT3, SAT 1 and SAT 2, Turkey 06 and other strains of lineage A). Non limiting examples of such heterologous antigens are illustrated in SEQ ID NO: 23 (Asia1-$A_{24}LL3B_{PVKV}3D_{YR}$) and SEQ ID NO: 24 (A/Turkey/06-$A_{24}LL3B_{PYKV}3D_{YR}$). Additionally, O1 campos-$A_{24}LL3B_{PVKV}3$ $D_{YR}$ (complete genome, also referred as O1campos), C3 Indaial-$A_{24}LL3B_{PVKV}3D_{YR}$ (complete genome), and capsid Argentina 2001 iso93 (capsid and 2A partial sequence) are provided in SEQ ID NOs 25, 26, and 27, respectively.

Variants of such antigens are also envisioned. The variants are at least 80% identical (e.g., 85% identical, 90% identical, 95% identical, 96% identical, 97% identical, 98% identical or 99% identical) to a reference sequence using one of the alignment programs described using standard parameters. Multiple alignment tools are available to determine sequence identity, including, without limitations, BLAST, CLUSTAL or PHILIP.

One of skill in the art will recognize that these values can be appropriately adjusted to determine corresponding identity of proteins encoded by two nucleotide sequences by taking into account codon degeneracy, amino acid similarity, reading frame positioning, and the like.

In certain embodiments, the variants encompass more than the specific exemplary nucleotide or amino acid sequences and include functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

The polypeptides of the invention may also be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired modified activities of the parent FMD virus. The mutations that will be made in the DNA encoding the variant must not place the sequence out of reading frame and preferably will not create complementary regions that could produce secondary mRNA structure.

Methods of growing and purifying the antigens suitable for the instant invention are well known in the art and include, without limitations, hollow fiber filtration and PEG precipitation. These methods yield somewhat different antigenic compositions. For example, in PEG precipitation, the antigenic composition is depleted of non-structural proteins. In other methods, such as, for example, hollow fiber filtration, the antigenic composition contains both structural and non-structural FMD proteins. Accordingly, in some embodiments, the FMD antigen comprises structural proteins. In other embodiments, such as, for example, where the FMD antigen is prepared by hollow fiber filtration, the FMD antigen comprises both structural and non-structural proteins, particularly 3D protein.

Using current vaccine platforms, devoid of intrinsic antigenic markers to differentiate vaccinated from infected animals, removal of non-structural proteins is desirable as this remains desirable due to the fact that presence of antibodies to non-structural protein identifies infected animals. However in the context of the FMDLL3B3D platform, the presence of non-structural protein in the antigen preparation does not preclude differentiation between vaccinated and infected animals. It is in this context that the present formulation of antigen including non-structural proteins and adjuvant provide both protection against clinical disease at lower doses than purified antigen formulations and also prevent more effectively the establishment of persistent infections in ruminants.

Compositions

The compositions of the present invention can be formulated following accepted convention to include acceptable carriers for animals, including humans, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

The compositions of the present invention can further comprise one or more additional immunomodulatory components such as, e.g., an additional adjuvant or cytokine, among others. Non-limiting examples of such additional adjuvants that can be used in the vaccine of the present invention include the RIBI adjuvant system (Ribi Inc., Hamilton, Mont.), Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Other immunomodulatory agents that can be included in the vaccine include, e.g., one or more interleukins, interferons, or other known cytokines.

The routes of administration for the adjuvant compositions include parenteral, oral, oronasal, intranasal, intratracheal, topical, subcutaneous, intramuscular, transcutaneous, intradermal, intraperitoneal, intraocular, intravenous, and lingual administration. Any suitable device may be used to administer the compositions, including syringes, droppers, needleless injection devices, patches, and the like. The route and device selected for use will depend on the composition of the adjuvant, the antigen, and the subject, and are well known to the skilled artisan.

In view of high infectivity of FMD, measures which need to be taken to contain and/or eliminate FMD outbreak are controlled by regulatory authorities, such as, for example, national Ministries of Agriculture and sanctioned by international organizations such as the OIE (International Office of Epizootics). The measures which need to be undertaken in connection with the outbreak may include, without limitations, standstill of animal movements, effective controls on the movement of animal products, including milk, meat, hide, etc, stamping-out policy (slaughter of the animals in affected herd, and, where appropriate, those in other herds which have been exposed to infection by direct animal to animal contact, or by indirect contact with the pathogen). Often the animals in the neighboring herds are vaccinated followed by slaughter.

The inventors have surprisingly discovered that certain immunogenic compositions described herein prevent persistence, which is defined as the presence or shedding of FMD for longer than 28 days after the infection. In certain embodiments, such immunogenic compositions comprise an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to at least 6 µg of FMD virus per dose.

In certain embodiments, antigen may be present in the amount equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

The invention, therefore, also provides a method of reducing frequency of FMD persistence in a ruminant infected with FMD comprising administering to said ruminant prior to the infection the immunogenic compositions which comprise an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD (Foot-and-Mouth Disease) antigen in the amount equivalent to at least 6 µg of FMD virus per dose.

In different embodiments, the amount of the antigen may be equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

Administration of these immunogenic compositions to ruminants (e.g., cattle, sheep, camels, etc.) allows for the change in herd management practices. In certain embodiments, the vaccinated members of the herd are not slaughtered after a suspected contact with FMD virus.

In alternative (or additional) embodiments, the vaccinated animals are kept in quarantine for a shorter time. Thus, in certain embodiments, the animals suspected of coming in contact with FMD may be kept in quarantine for less than 30 days, e.g., 28 days, or 29 days.

Further, designation of an area as a containment zone means severe limitations of prohibition on movement of animals or animal products from the containment zone, generally, 30 days or more. Thus, in certain embodiments, the animals suspected of coming in contact with FMD may be moved from the containment zone within less than 30 days, e.g., 28 days or 29 days from the suspected contact with FMD.

In the embodiments where the antigen component entails a genetically engineered FMD antigen, e.g., as described above, it is possible to differentiate vaccinated from infected animals. Therefore, in additional embodiments, the herd management methods (or method of reducing frequency of FMD persistence in a ruminant infected with FMD).

In other words, the immunogenic compositions, in certain embodiments comprising an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to at least 6 µg of FMD virus per dose may be used for herd management wherein, upon suspected contact with FMD infection, the vaccinated members of said herd are not slaughtered; and/or quarantined for 0-30 days after the suspected contact and/or moved beyond the infected premises within 30 days of the suspected contact.

In different embodiments, the amount of the antigen may be equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

The invention will be further described in the following non-limiting examples.

EXAMPLES

Example 1. Preparation of Antigens

Two methods were used to prepare the antigens: Hollow Fiber Filtration and PEG precipitation.

PEG (poly-ethylene glycol) precipitation methods have been known in the art. Briefly, BHK-21 cells were infected with the FMD virus. Then (24-36 h later) the cells were lysed by freeze-thawing, and cell lysate was clarified of cell debris by low speed centrifugation (500×g). PEG was added (8% w/v) to the supernatant containing both structural and non-structural proteins. The mixture was incubated for 12-18 hr at 4° C. During this incubation, FMDV particles associate with the PEG. Antigen was recovered by centrifugation at 16,000×g and collection of the precipate pellet containing PEG and virus. The supernatant, containing cellular and viral non-structural proteins was discarded. The pellet, to which the virus particles are bound, was then washed with small volumes of buffer to elute the FMDV particles from the PEG.

An additional method described herein is based on hollow-fiber concentration, of FMDV culture supernatants. The steps of this method consist of successive filtration arrangement to remove first the cell debris and large material from the cultures (BHK-21 cells infected with the FMD virus and lysed by freeze-thawing). The culture material was pumped successively through a 10 µm capsule filter, a 4.5 µm capsule filter, then finally through a 0.8 µm/0.2 µm filter. This filtrate was then concentrated using a hollow fiber ultrafiltration cartridge that allows particles smaller than 0.01 µm to flow through the membrane. FMDV particles and many non-structural proteins remain in the column circuit while liquid and smaller proteins go through the membrane into the waste. The column circuit was run until the concentrate reaches the desired volume, normally a ten-fold concentration.

FIG. 1 is a Western blot illustrating the difference in quality between the PEG precipitated and hollow fiber concentrated antigens. Hollow fiber concentrated antigen contains large amounts of structural and non structural proteins as illustrated in this FIGURE by western blot staining using an antibody specific for protein 3D, the largest FMDV non-structural proteins and antibody specific to capsid protein (structural protein). In contrast, PEG-precipitated antigens (lane 9) contained structural protein but did not contain detectable levels of 3D protein.

Example 2. Effects of FMD Vaccines Adjuvanted with TXO

Animals and Sample Collection

Six- to eight-month-old Holstein steers weighing 180-230 kg were used in this study. The animals were free of FMDV-reactive antibodies as determined by 3D ELISA test prior to vaccination as determined later from serum samples taken on Day 0. All 28 animals were commingled in one room in a BSL-3-Ag animal testing facility. The animals were fed complete ration pellets or alfalfa cubes, with water and salt blocks available ad libitum. Animals were acclimatized five days to the facilities prior to Day 0. Animals were previously treated with Bovi-Shield GOLD® 5, Micotil® 300, LiquamycieLA−200° and Dectomax®. Groups of animals (n=4 each) with consecutive ear tag numbers were assigned to a treatment group.

No adverse events were documented following vaccination.

Serum separator blood tubes to obtain serum samples were collected at Days 0 (before vaccination), 4, 7, 14, 21 (before challenge), 24, 28, 31 and 42 from all animals. The serum samples were kept frozen until tested for the presence of neutralizing antibodies against FMDV in a serum neutralization assay (reported as the reciprocal of the last serum dilution to neutralize 100 $TCID_{50}$ of homologous FMDV in 50% of the wells) or to study the anti-3Dpol response (by means of a competitive Enzyme-Linked Immunosorbent Assay).

As recommended by the OIE ("Manual of Diagnostic Tests and Vaccines for Terrestrial Animals"), challenge of vaccinated cattle for vaccine efficacy was by needle inoculation by the intradermal lingual (IDL) route. At 21 days post-vaccination, all vaccinated and naïve animals were inoculated IDL with 10,000 $BTID_{50}$ (50% bovine tongue infectious doses) of homologous FMDV A24 Cruzeiro divided as 4 inoculations of 0.1 ml/each with 2,500 $BTID_{50}$/0.1 ml. All animals were followed for 10 days post-challenge to assess development of clinical disease as expressed by fever, nasal secretion, salivation, loss of appetite and/or lameness. Clinical evaluation for the presence of hoof vesicles was performed with sedation (xylazine given IM at 0.22 mg/kg so as to maintain sternal recumbency for the duration of the procedure) at day 21 (before inoculation) and days 24, 28 and 31. The sedative was reversed with tolazoline, IV, at a dose of 2 mg/kg.

Vaccines

Antigens were prepared as described in Example 1. Antigen stock solutions contained 5.51 μg/ml antigen prepared by hollow fiber filtertration (Prep A) or 10.26 μg/ml antigen prepared by PEG precipitation (Prep B).

The details of the immunogenic compositions administered to the animals are provided in Table 1. Each group contained four animals.

TABLE 1

Study Design

| Group | Antigen | Amount/5 ml | Adjuvant/5 ml | Volume injected, ml, IM |
|---|---|---|---|---|
| T01 | None | N/A | PBS (Neg control) | 5 |
| T02 | FMDV (Prep B)-PEG ppt. | 8 μg | Light Mineral oil - SPAN ®80 | 5 |
| T03 | FMDV (Prep B) PEG ppt. | 2 μg | TWEEN ®80 DEAE Dextran | 1.25 |
| T04 | FMDV (Prep B)-PEG ppt. | 0.5 μg | (100 mg); SEQ ID NO: | 0.3125 |
| T05 | FMDV (Prep A)-Hollow fiber filt.- | 8 μg | 8; 75% pure: 100 μg | 5 |
| T06 | FMDV (Prep A)-Hollow fiber filt. | 2 μg | | 1.25 |
| T07 | FMDV (Prep A)-Hollow fiber filt. | 0.5 μg | | 0.3125 |

The immunogenic compositions of groups T02 through T06 were homogenized on the day of vaccination and administered to the animals on Day 0.

Persistence was measured as the presence or absence of virus (either FMDV viral RNA and/or infectious FMDV) determined using both viral isolation and quantitative rRT-PCR. The primers used for the quantitative rRT-PCR were as follows:

```
Forward (SEQ ID NO: 28):
GACAAAGGTTTTGTTCTTGGTCA

Reverse (SEQ ID NO: 29):
TGCGAGTCCTGCCACGGA

Taqman probe: (FAM reporter, TAMRA quencher,
SEQ ID NO: 30)
TCCTTTGCACGCCGTGGGAC
```

Serum neutralizing titers to FMDV are summarized in Table 2.

TABLE 2

Serum Neutralizing Titers

| Treatment | Serum Neutralizing Titer Day 0 | Day 21 | Day 42 |
|---|---|---|---|
| T01 | $0.45^{a}$ | $0.45^{a}$ | $2.62^{ab}$ |
| T02 | $0.45^{a}$ | $1.64^{c}$ | $2.84^{b}$ |
| T03 | $0.45^{a}$ | $0.90^{b}$ | $2.39^{ab}$ |
| T04 | $0.45^{a}$ | $0.76^{b}$ | $2.74^{ab}$ |
| T05 | $0.45^{a}$ | $1.55^{c}$ | $2.28^{a}$ |
| T06 | $0.45^{a}$ | $0.81^{b}$ | $2.36^{ab}$ |
| T07 | $0.45^{a}$ | $0.54^{a}$ | $2.68^{ab}$ |

[a,b,c]Treatment groups with same letter within each day are not significantly different at alpha = 0.05

Signs of FMDV were scored as presence (1) or absence (0) of hoof vesicles, i.e., a presence of a vesicle on a single hoof produced the score of 1, the presence of vesicles on only 2 hooves produced score of 2 and vesicles on all 4 hooves produced a score of 4. Once an animal received a score of 4, it was considered to have a score of 4 for the duration of the study.

The scores from individual animals for each hoof and for each day of examination are shown in Table 3. In Table 4, a summary of each animal's scores according to whether any hoof was positive is presented.

TABLE 3

FMDV Vesicle Scoring individual Animal Listing

| Treatment | Animal | Day of Study 21 Location | | | | Day of Study 24 Location | | | |
|---|---|---|---|---|---|---|---|---|---|
| | | LEFT FORE | LEFT REAR | RIGHT FORE | RIGHT REAR | LEFT FORE | LEFT REAR | RIGHT FORE | RIGHT REAR |
| T01 | R14-84 | 0 | 0 | 0 | 0 | 0 | 1 | 0 | 1 |
| | R14-85 | 0 | 0 | 0 | 0 | 1 | 1 | 1 | 1 |
| | R14-86 | 0 | 0 | 0 | 0 | 0 | 1 | 0 | 0 |
| | R14-87 | 0 | 0 | 0 | 0 | 1 | 1 | 1 | 1 |
| T02 | R14-72 | 0 | 0 | 0 | 0 | 0 | 0 | 0 | 0 |
| | R14-73 | 0 | 0 | 0 | 0 | 0 | 0 | 0 | 0 |
| | R14-74 | 0 | 0 | 0 | 0 | 0 | 0 | 0 | 0 |
| | R14-75 | 0 | 0 | 0 | 0 | 0 | 0 | 0 | 0 |
| T03 | R14-76 | 0 | 0 | 0 | 0 | 0 | 0 | 0 | 0 |
| | R14-77 | 0 | 0 | 0 | 0 | 0 | 1 | 0 | 0 |
| | R14-78 | 0 | 0 | 0 | 0 | 0 | 0 | 0 | 0 |
| | R14-79 | 0 | 0 | 0 | 0 | 0 | 0 | 0 | 0 |
| T04 | R14-80 | 0 | 0 | 0 | 0 | 0 | 0 | 0 | 0 |
| | R14-81 | 0 | 0 | 0 | 0 | 0 | 0 | 0 | 0 |
| | R14-82 | 0 | 0 | 0 | 0 | 0 | 0 | 0 | 0 |
| | R14-83 | 0 | 0 | 0 | 0 | 0 | 0 | 0 | 0 |
| T05 | R14-60 | 0 | 0 | 0 | 0 | 0 | 0 | 0 | 0 |
| | R14-61 | 0 | 0 | 0 | 0 | 0 | 0 | 0 | 0 |
| | R14-62 | 0 | 0 | 0 | 0 | 0 | 0 | 0 | 0 |
| | R14-63 | 0 | 0 | 0 | 0 | 0 | 0 | 0 | 0 |
| T06 | R14-64 | 0 | 0 | 0 | 0 | 0 | 0 | 0 | 0 |
| | R14-65 | 0 | 0 | 0 | 0 | 0 | 0 | 0 | 0 |
| | R14-66 | 0 | 0 | 0 | 0 | 0 | 0 | 0 | 0 |
| | R14-67 | 0 | 0 | 0 | 0 | 0 | 0 | 0 | 0 |
| T07 | R14-68 | 0 | 0 | 0 | 0 | 0 | 0 | 0 | 0 |
| | R14-69 | 0 | 0 | 0 | 0 | 0 | 0 | 0 | 0 |
| | R14-70 | 0 | 0 | 0 | 0 | 0 | 0 | 0 | 0 |
| | R14-71 | 0 | 0 | 0 | 0 | 0 | 0 | 0 | 0 |

TABLE 3-continued

FMDV Vesicle Scoring individual Animal Listing

| | | Day of Study | | | | | | | |
| --- | --- | --- | --- | --- | --- | --- | --- | --- | --- |
| | | 28 Location | | | | 31 Location | | | |
| Treatment | Animal | LEFT FORE | LEFT REAR | RIGHT FORE | RIGHT REAR | LEFT FORE | LEFT REAR | RIGHT FORE | RIGHT REAR |
| T01 | R14-84 | 1 | 1 | 1 | 1 | 1* | 1* | 1* | 1* |
| | R14-85 | 1* | 1* | 1* | 1* | 1* | 1* | 1* | 1* |
| | R14-86 | 1 | 1 | 1 | 1 | 1* | 1* | 1* | 1* |
| | R14-87 | 1* | 1* | 1* | 1* | 1* | 1* | 1* | 1* |
| T02 | R14-72 | 0 | 0 | 0 | 0 | 0 | 0 | 0 | 0 |
| | R14-73 | 0 | 0 | 0 | 0 | 0 | 0 | 0 | 0 |
| | R14-74 | 0 | 0 | 0 | 0 | 0 | 0 | 0 | 0 |
| | R14-75 | 0 | 0 | 0 | 0 | 0 | 0 | 0 | 0 |
| T03 | R14-76 | 0 | 0 | 0 | 0 | 0 | 0 | 0 | 0 |
| | R14-77 | 0 | 1 | 0 | 0 | 0 | 1 | 0 | 0 |
| | R14-78 | 0 | 0 | 0 | 0 | 0 | 0 | 0 | 0 |
| | R14-79 | 0 | 0 | 0 | 0 | 0 | 0 | 0 | 0 |
| T04 | R14-80 | 0 | 0 | 0 | 0 | 0 | 0 | 0 | 0 |
| | R14-81 | 0 | 0 | 0 | 0 | 0 | 0 | 0 | 0 |
| | R14-82 | 0 | 0 | 0 | 0 | 0 | 0 | 0 | 0 |
| | R14-83 | 0 | 0 | 0 | 0 | 0 | 0 | 0 | 0 |
| T05 | R14-60 | 0 | 0 | 0 | 0 | 0 | 0 | 0 | 0 |
| | R14-61 | 0 | 0 | 0 | 0 | 0 | 0 | 0 | 0 |
| | R14-62 | 0 | 0 | 0 | 0 | 0 | 0 | 0 | 0 |
| | R14-63 | 0 | 0 | 0 | 0 | 0 | 0 | 0 | 0 |
| T06 | R14-64 | 0 | 0 | 0 | 0 | 0 | 0 | 0 | 0 |
| | R14-65 | 0 | 0 | 0 | 0 | 0 | 0 | 0 | 0 |
| | R14-66 | 0 | 0 | 0 | 0 | 0 | 0 | 0 | 0 |
| | R14-67 | 0 | 0 | 0 | 0 | 0 | 0 | 0 | 0 |
| T07 | R14-68 | 0 | 0 | 0 | 0 | 0 | 0 | 0 | 0 |
| | R14-69 | 0 | 0 | 0 | 0 | 0 | 0 | 0 | 0 |
| | R14-70 | 0 | 0 | 0 | 0 | 0 | 0 | 0 | 0 |
| | R14-71 | 0 | 0 | 0 | 0 | 0 | 0 | 0 | 0 |

*Automatically scored as a '1' since all hooves for this animal previously had vesicles on all

TABLE 4

FMDV Vesicle Scoring - Any Hoof Location Positive

| Treatment | Animal | Day of Study 21 | 24 | 28 | 31 |
|---|---|---|---|---|---|
| T01 | R14-84 | No | Yes | Yes | Yes* |
|  | R14-85 | No | Yes | Yes* | Yes* |
|  | R14-86 | No | Yes | Yes | Yes* |
|  | R14-87 | No | Yes | Yes* | Yes* |
| T02 | R14-72 | No | No | No | No |
|  | R14-73 | No | No | No | No |
|  | R14-74 | No | No | No | No |
|  | R14-75 | No | No | No | No |
| T03 | R14-76 | No | No | No | No |
|  | R14-77 | No | Yes | Yes | Yes |
|  | R14-78 | No | No | No | No |
|  | R14-79 | No | No | No | No |
| T04 | R14-80 | No | No | No | No |
|  | R14-81 | No | No | No | No |
|  | R14-82 | No | No | No | No |
|  | R14-83 | No | No | No | No |
| T05 | R14-60 | No | No | No | No |
|  | R14-61 | No | No | No | No |
|  | R14-62 | No | No | No | No |
|  | R14-63 | No | No | No | No |
| T06 | R14-64 | No | No | No | No |
|  | R14-65 | No | No | No | No |
|  | R14-66 | No | No | No | No |
|  | R14-67 | No | No | No | No |
| T07 | R14-68 | No | No | No | No |
|  | R14-69 | No | No | No | No |
|  | R14-70 | No | No | No | No |
|  | R14-71 | No | No | No | No |

*Automatically scored as Yes since all hooves for this animal previously had vesicles on all four hooves All animals in T01 (negative control) exhibited hoof vesicles starting on Day 24. On Days 28 and 31, all hooves in all T01 animals were found to have vesicles. In contrast, full protection (i.e., no hoof vesicles) was observed for every group except T03 (2 μg dose of FMDV precipitated with PEG), where one animal (R14-77) received the score of 1 at Days 24, 28, and 31. The effects of the tested immunogenic compositions on persistent infection are illustrated in Tables 5 and 6. Persistence was defined as presence of infectious virus or viral RNA in oesophageal-pharyngeal fluid (obtained using a "Probang" cup) after 28 days post-challenge (day 49 after vaccination, as shown in tables 5 and 6). In Table 5, quantitative rRT-PCR results for individual animals and treatment group back-transformed least square means of FMDV RNA copy numbers per mL from probang samples are shown. In Table 6, results of probang sample virus isolation testing are reported as either positive or negative. The values below 1.87 in table 5 were scored as 'negative' due to limit of detection of the assay.

TABLE 5

Probang rRT-PCR Individual Animal Listing and Back-Transformed Least Squares Means per Treatment Group

| Treatment Number | Animal | Day 38 Test Result | Day 42 Test Result | Day 49 Test Result | Day 52 Test Result |
|---|---|---|---|---|---|
| T01 | R14-84 | 4.29 | 4.72 | <1.87 | 3.83 |
| T01 | R14-85 | 4.26 | 6.01 | 5.14 | 4.7 |
| T01 | R14-86 | <1.87 | 3.62 | <1.87 | <1.87 |
| T01 | R14-87 | <1.87 | <1.87 | <1.87 | <1.87 |
| Group Mean |  | 1.999 | 3.130 | 1.432 | 1.992 |
| T02 | R14-72 | <1.87 | <1.87 | <1.87 | <1.87 |
| T02 | R14-73 | <1.87 | <1.87 | <1.87 | <1.87 |
| T02 | R14-74 | <1.87 | <1.87 | <1.87 | <1.87 |
| T02 | R14-75 | <1.87 | <1.87 | <1.87 | <1.87 |
| Group Mean |  | 0.935 | 0.935 | 0.935 | 0.935 |
| T03 | R14-76 | 4.98 | 4.68 | <1.87 | <1.87 |
| T03 | R14-77 | 5.52 | 3.43 | <1.87 | <1.87 |
| T03 | R14-78 | <1.87 | 4.35 | <1.87 | 5.3 |
| T03 | R14-79 | <1.87 | <1.87 | <1.87 | <1.87 |
| Group Mean |  | 2.214 | 2.843 | 0.935 | 1.443 |
| T04 | R14-80 | <1.87 | <1.87 | 4.88 | 4.59 |
| T04 | R14-81 | 5.08 | 4.01 | 3.98 | 4.65 |
| T04 | R14-82 | <1.87 | 4.47 | 6.12 | 4.32 |
| T04 | R14-83 | <1.87 | <1.87 | <1.87 | <1.87 |
| Group Mean |  | 1.427 | 1.990 | 3.247 | 3.047 |
| T05 | R14-60 | <1.87 | <1.87 | <1.87 | <1.87 |
| T05 | R14-61 | <1.87 | <1.87 | <1.87 | <1.87 |
| T05 | R14-62 | 4.75 | <1.87 | <1.87 | <1.87 |
| T05 | R14-63 | <1.87 | <1.87 | <1.87 | <1.87 |
| Group Mean |  | 1.404 | 0.935 | 0.935 | 0.935 |
| T06 | R14-64 | <1.87 | <1.87 | <1.87 | <1.87 |
| T06 | R14-65 | 4.10 | 4.11 | <1.87 | 3.39 |
| T06 | R14-66 | <1.87 | <1.87 | <1.87 | <1.87 |
| T06 | R14-67 | 4.14 | 5.08 | 5.18 | 4.82 |
| Group Mean |  | 1.963 | 2.067 | 1.434 | 1.944 |
| T07 | R14-68 | <1.87 | <1.87 | <1.87 | <1.87 |
| T07 | R14-69 | <1.87 | <1.87 | <1.87 | <1.87 |
| T07 | R14-70 | <1.87 | <1.87 | <1.87 | <1.87 |
| T07 | R14-71 | 5.34 | 5.46 | 4.49 | 3.7 |
| Group Mean |  | 1.445 | 1.453 | 1.384 | 1.319 |

TABLE 6

Probang Sample Virus Isolation - Individual Animal Listing

| Treatment | Animal | Day of Study 38 | 42 | 49 | 52 |
|---|---|---|---|---|---|
| T01 | R14-84 | Pos | Pos | Pos | Pos |
|  | R14-85 | Pos | Pos | Pos | Pos |
|  | R14-86 | Neg | Neg | Neg | Neg |
|  | R14-87 | Neg | Neg | Neg | Neg |
| T02 | R14-72 | Neg | Neg | Neg | Neg |
|  | R14-73 | Neg | Neg | Neg | Neg |
|  | R14-74 | Neg | Pos | Neg | Neg |
|  | R14-75 | Neg | Neg | Neg | Neg |
| T03 | R14-76 | Pos | Pos | Neg | Pos |
|  | R14-77 | Pos | Pos | Neg | Neg |
|  | R14-78 | Pos | Pos | Pos | Pos |
|  | R14-79 | Neg | Neg | Neg | Neg |
| T04 | R14-80 | Neg | Neg | Pos | Pos |
|  | R14-81 | Pos | Pos | Pos | Pos |
|  | R14-82 | Pos | Pos | Pos | Pos |
|  | R14-83 | Pos | Pos | Pos | Pos |
| T05 | R14-60 | Neg | Neg | Neg | Neg |
|  | R14-61 | Neg | Neg | Neg | Neg |
|  | R14-62 | Neg | Neg | Neg | Neg |
|  | R14-63 | Neg | Neg | Neg | Neg |
| T06 | R14-64 | Neg | Neg | Neg | Neg |
|  | R14-65 | Pos | Pos | Pos | Pos |
|  | R14-66 | Neg | Neg | Neg | Neg |
|  | R14-67 | Pos | Pos | Pos | Pos |
| T07 | R14-68 | Neg | Neg | Neg | Neg |
|  | R14-69 | Neg | Neg | Neg | Neg |
|  | R14-70 | Neg | Neg | Neg | Neg |
|  | R14-71 | Pos | Pos | Pos | Pos |

For Group 1 (saline control), three animals were positive at least once for FMDV by rRT-PCR and two animals were always positive for virus isolation.

In Group T02, no animal was ever found to be carrying FMDV by rRT-PCR, but one animal (R14-74) was found to be positive by virus isolation assay at a single time point only (Day 42: day 21 post-challenge) but negative thereafter (Days 49: and 52, indicating the absence of persistent infection. The other animals in T02 did not carry FMDV detectable either by rRT-PCR or by viral isolation assay at day 38 and beyond.

In group T03, one animal (R14-79) was fully protected from FMDV infection, two animals demonstrated the presence of FMDV (either by rRT-PCR or by viral isolation assay) on three or four of the testing days and one animal (R14-77) demonstrated FMDV presence by both tests on Days 38 and 42, but not thereafter.

In group T04, all four animals exhibited persistence of FMDV by one or both tests through Day 52.

In Group T05, one animal (R14-62) demonstrated the presence of the virus only on Day 38 by rRT-PCR but not by virus isolation and and virus was not detected by either test thereafter. FMDV was not detected either by rRT-PCR or by viral isolation assay at any time for the other three animals in group T05.

In Group T06, two animals were fully protected from persistence while the other two were either rRT-PCR or virus isolation positive at every time point examined.

In group T07, three out of four animals were fully protected while one animal (R14-71) was positive for both rRT-PCR and virus isolation at each time point.

Table 7 summarizes the results of persistence experiments. Animals were considered as non-persistent if neither rRT-PCR or viral isolation assays detected FMDV on both day 49 (28 days post-challenge) and day 52 (31 day post-challenge).

TABLE 7

Frequency of Persistence and Non-Persistence

| Treatment | Persistent % | Not Persistent % |
| --- | --- | --- |
| T01 (saline) | 50 | 50 |
| T02 (FMDV PEG ppt - 8 µg) | 0 | 100 |
| T03 (FMDV PEG ppt - 2 µg) | 50 | 50 |
| T04 (FMDV PEG ppt - 0.5 µg) | 100 | 0 |
| T05 (FMDV Hollow fiber - 8 µg) | 0 | 100 |
| T06 (FMDV Hollow fiber - 2 µg) | 50 | 50 |
| T07 (FMDV Hollow fiber - 0.5 µg) | 25 | 75 |

Only two of the eight animals administered 8 µg of antigen (Groups T02 and T05) ever exhibited the presence of virus and that was for one day only (one each on Days 37 and 42). The other animals in these groups were fully protected Considering that the virus presence was not detected on both 28 and 31 days after infection, none of the animals administered 8 µg of antigen was considered to be persistently infected. Five out of eight animals administered 2 µg of antigen (Groups T03 and T06) exhibited viral persistence. Four out of eight animals eight animals administered 0.5 µg of antigen (Groups T04 and T07) exhibited persistence.

Taken together, these results indicate protection from FMDV viral persistence in animals administered 8 µg antigen, and it also appears that the purification of the antigen by hollow fiber filtration is advantageous compared to PEG precipitation. The main difference between the two antigen formulations is the presence of non-structural proteins in addition to structural ones in the hollow fiber filtration formulation. Thus, without being bound by theory, it appears that the quality of the immune response elicited by vaccines where the antigen contains both structural and non-structural proteins, and particularly protein 3D, are more effective in preventive FMDV persistence, as illustrated in Table 8.

TABLE 8

Effect of antigen preparation method on immune response.

| Treatment | Persistent % | Not Persistent % |
| --- | --- | --- |
| T01 (saline) | 50% (2 out of 4) | 50% (2 out of 4) |
| Prep A (hollow fiber, groups T05-T07 Combined) | 25% (3 out of 12) | 75% (9 out of 12) |
| Prep B (PEG precipitation, groups T02-T04 Combined) | 50% (6 out of 12) | 50% (6 out of 12) |

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. An immunogenic composition comprising an antigen component and an adjuvant component, wherein
   a) the adjuvant component comprises an emulsion containing oil, an immunostimulatory oligonucleotide, and diethylaminoethyl (DEAE) Dextran and
   b) the antigen component comprises 0.5-10 µg or 6-20 µg of FMD (Foot-and-Mouth Disease) virus composition per dose.

2. The immunogenic composition of claim 1, wherein the immunostimulatory oligonucleotide comprises CpG.

3. The immunogenic composition of claim 1, wherein the immunostimulatory oligonucleotide comprises at least 15 contiguous nucleotides of SEQ ID NO: 8.

4. The immunogenic composition of claim 1, wherein said oily phase is present in the amount of up to 80% v/v of the composition.

5. The immunogenic composition of claim 1, wherein the oily phase comprises 50.01%-55% v/v of the composition.

6. The immunogenic composition of claim 1, wherein the adjuvant component comprises SEQ ID NO: 8 and diethylaminoethyl (DEAE) Dextran.

7. The immunogenic composition of claim 6, wherein the DEAE Dextran is present in the amount of 6-200 mg per dose.

8. The immunogenic composition of claim 7, wherein the immunostimulatory oligonucleotide is present in the amount of 6-200 µg per dose.

9. The immunogenic composition of claim 1, wherein said FMD virus composition is a preparation of FMD virus Cruzeiro strain.

10. The immunogenic composition of claim 9, wherein said FM D virus Cruzeiro strain is genetically engineered.

11. The immunogenic composition of claim 10, wherein said FMD virus Cruzeiro strain contains a deletion of the leader coding region (LL).

12. The immunogenic composition of claim 11, wherein said FMD virus Cruzeiro strain contains negative antigenic markers introduced in one or both of the viral non-structural $3DP^{pol}$ and 3B proteins.

13. The immunogenic composition of claim 10, wherein said FMD virus Cruzeiro strain contains a heterologous capsid protein.

14. The immunogenic composition of claim 13, wherein the heterologous capsid protein is from a strain selected from Asia1, Turkey06, O1Campos, C3Indaial, and A2001-Argentina.

15. An immunogenic composition according to claim 13, comprising DEAE Dextran in the amount of 6-200 mg per dose, and the immunostimulatory oligonucleotide comprising at least 15 contiguous nucleotides of SEQ ID NO: 8 is present in the amount of 6-200 µg per dose.

16. A method of preventing FMD in an animal in need thereof, comprising administering to said animal the immunogenic composition according to claim 15.

17. The immunogenic composition of claim 1, wherein the antigen component comprises
   a) 0.5-6 µg of FMD virus per dose; or
   b) 0.5-4 µg of FMD virus per dose; or
   c) 0.5-2 µg of FMD virus per dose; or
   d) 0.5-1.5 µg of FMD virus per dose; or
   e) 6-20 µg of FMD virus per dose; or
   f) 6-20 µg of FMD virus per dose; or
   g) 8-20 µg of FMD virus per dose; or
   h) 8-12 µg of FMD virus per dose; or
   i) 6-18 µg of FMD virus per dose.

18. A method of preventing FMD in an animal in need thereof, comprising administering to said animal the immunogenic composition according to claim 1.

19. The method according to claim 18, wherein the FMD virus composition is prepared by hollow fiber filtration.

* * * * *

SEQUENCE LISTING

<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 1
tcgtcgacga tcggcgcgcg ccg    23

<210> SEQ ID NO 2
<211> LENGTH: 23

```
<212> TYPE: DNA
<213> ORGANISM: Artificial Sequence
<220> FEATURE:
<223> OTHER INFORMATION: CpG oligonucleotide

<400> SEQUENCE: 2
tcgacgtcga tcggcgcgcg ccg                                      23

<210> SEQ ID NO 3
<211> LENGTH: 24
<212> TYPE: DNA
<213> ORGANISM: Artificial Sequence
<220> FEATURE:
<223> OTHER INFORMATION: CpG oligonucleotide

<400> SEQUENCE: 3
tcgacgtcga tcggcgcgcg ccgt                                     24

<210> SEQ ID NO 4
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 4
ncgacgtcga tcggcgcgcg ccg                                      23

<210> SEQ ID NO 5
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 5
ncgacgtcga tcggcgcgcg ccgt                                     24

<210> SEQ ID NO 6
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 6
ncgacgtcga tcggcgcgcg ccgt                                     24

<210> SEQ ID NO 7
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
```

<223> OTHER INFORMATION: 5'-Ethyl-2'-deoxyuridine

<400> SEQUENCE: 7
ncgacgtcga tcggcgcgcg ccg                                              23

<210> SEQ ID NO 8
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 8
ncgtcgacga tcggcggccg ccgt                                             24

<210> SEQ ID NO 9
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 9
ncgtcgacga tcggcggccg ccgt                                             24

<210> SEQ ID NO 10
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 10
tcgtcgacga tcggcgcgcg ccg                                              23

<210> SEQ ID NO 11
<211> LENGTH: 20
<212> TYPE: DNA
<213> ORGANISM: Artificial Sequence
<220> FEATURE:
<223> OTHER INFORMATION: RNA

<400> SEQUENCE: 11
uuguuguugu uguuguuguu                                                  20

<210> SEQ ID NO 12
<211> LENGTH: 20
<212> TYPE: DNA
<213> ORGANISM: Artificial Sequence
<220> FEATURE:
<223> OTHER INFORMATION: RNA

<400> SEQUENCE: 12
uuauuauuau uauuauuauu                                                  20

<210> SEQ ID NO 13
<211> LENGTH: 19
<212> TYPE: DNA
<213> ORGANISM: Artificial Sequence

```
<220> FEATURE:
<223> OTHER INFORMATION: RNA

<400> SEQUENCE: 13
aaacgcucag ccaaagcag                                                    19

<210> SEQ ID NO 14
<211> LENGTH: 21
<212> TYPE: DNA
<213> ORGANISM: Artificial Sequence
<220> FEATURE:
<223> OTHER INFORMATION: DNA/RNA
<220> FEATURE:
<221> NAME/KEY: misc_feature
<222> LOCATION: (11)..(17)
<223> OTHER INFORMATION: ribonucleotides

<400> SEQUENCE: 14
tcgtcgtttt guuguguttt t                                                 21

<210> SEQ ID NO 15
<211> LENGTH: 10867
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 15
ggggccggcc aatccagtcc ggcgaccggc tcgcagaacc aatctggcaa cactggcagc      60
ataattaaca actactacat gcagcaatac cagaactcca tggacacaca gttgggagac     120
aatgccatca gtggaggctc caacgagggc tccacggaca caacttcaac acacacaacc     180
aacactcaaa acaatgactg gttctcgaag ctcgccagtt cagcttttac cggtctgttc     240
ggtgcactgc tcgccgacaa gaagacagag gaaacgacac ttcttgagga ccgcatcctc     300 accaccccgca acgggcacac cacctcgacg acccaatcga gtgtgggtgt cacacacggg     360
tactccacag aggaggacca cgttgctggg cccaacacat cgggcctgga gacgcgagtg     420
gtgcaggcag agagattcta caaaaagtac ttgtttgact ggacaacgga caaggcattt     480
ggacacctgg aaaagctgga gctcccgtcc gaccaccacg gtgtctttgg acacttggtg     540
gactcgtacg cctatatgag aaatggctgg gatgttgagg tgtccgctgt tggcaaccag     600
ttcaacggcg ggtgcctcct ggtggccatg gtacctgaat ggaaggaatt tgacacacgg     660
gagaaatacc aactcaccct tttcccgcac cagtttatta gccccagaac taacatgact     720
gcccacatca cggtccccta ccttggtgtg aacaggtatg atcagtacaa gaagcataag     780
ccctggacat tggttgtcat ggtcgtgtcg ccacttacgg tcaacaacac tagtgcggca     840
caaatcaagg tctacgccaa catagctccg acctatgttc acgtggccgg tgaactcccc     900
tcgaaagagg ggatttttcc ggttgcatgt gcggacggtt acggaggatt ggtgacgaca     960
gacccgaaga cagctgaccc tgcttatggc aaggtgtaca ccccgccta gactaactac    1020 cctgggcgct tcaccaacct gttggacgtg gccgaagcgt gtcccacttt cctctgcttt    1080
gacgacggga aaccgtacgt caccacgcgc acggatgaca cccgactttt ggccaagttt    1140
gacctttccc ttgccgcaaa acatatgtcc aacacatacc tgtcagggat tgctcagtac    1200
tacacacagt actctggcac catcaatttg catttcatgt tcacaggttc cactgattca    1260
aaggcccgat acatggtggc ctacatccca cctggggtgg agacaccacc ggacacacct    1320
gaaagggctg cccactgcat tcacgctgaa tgggacactg gactaaactc caaattcact    1380
```

```
ttctcaatcc cgtacgtatc cgccgcggat tacgcgtaca cagcgtctga cacggcagaa    1440
acaatcaacg tacagggatg ggtctgcatc taccaaatta cacacgggaa ggctgaaaat    1500
gacaccttgg tcgtgtcggt tagcgccggc aaagactttg agttgcgcct cccgattgac    1560
ccccgccagc agaccaccgc taccggggaa tcagcagacc cggtcaccac caccgtggag    1620
aactacggcg gtgagacaca aatccagaga cgtcaccaca cggacattgg tttcatcatg    1680
gacagatttg tgaagatcca aagcttgagc ccaacacatg tcattgacct catgcagact    1740
caccaacacg gtctggtggg tgccttgctg cgtgcagcca cgtactactt ttctgacctg    1800
gaaattgttg tacggcacga aggcaatctg acctgggtgc ccaacggcgc ccctgaatca    1860
gccctgttga acaccagcaa ccccactgcc tacaacaagg caccattcac gagactcgct    1920 ctccectaca ctgcgccgca ccgtgtgctg caacagtgt acaacgggac gagtaagtat      1980
gctgtgggtg gttcaggcag aagaggcgac atggggtctc tcgcggcgcg agtcgtgaaa    2040
cagcttcctg cttcatttaa ctacggtgca atcaaggccg acgccatcca cgaacttctc    2100
gtgcgcatga acgggccga gctctactgc cccagaccgc tgttggcaat agaggtgtct      2160
tcgcaagaca ggcacaagca aaagatcatt gcaccagcaa agcagcttct gaattttgac    2220
ctgcttaagc tagccggaga cgttgagtcc aaccctgggc ccttcttctt ctccgacgtt    2280
aggtcaaact tttccaagct ggtagacaca atcaaccaga tgcaggaaga catgtccaca    2340
aagcacggac ctgactttaa ccggttggtg tccgcttttg aggagttggc cactggagtg    2400
aaagccatca ggaccggtct tgacgaggcc aagccctggt acaagcttat caagctcctg    2460
agccgcctgt cgtgcatggc cgctgtggca gcacggtcaa aggacccagt ccttgtggcc    2520
atcatgctgg ctgacaccgg tctcgagatt ctggacagca ccttcgtcgt gaagaagatc    2580
tccgactcgc tctccagtct cttccacgtg ccggccccg tcttcagttt cggagccccg       2640
attctgttag ccgggttggt caaggtcgcc tcgagtttct tccggtccac gcccgaagac    2700
cttgagagag cagagaaaca gctcaaagca cgtgacatca cgacattttt cgccattctc    2760
aagaacggcg agtggctggt caaattgatc cttgccatcc gcgactggat caaggcatgg    2820
atagcctcag aagaaaagtt tgtcaccacg acagacttgg tacctagcat ccttgaaaaa    2880
cagcaggacc tcaacgaccc aagcaagtac aaggaagcca aggagtggct cgacaacgcg    2940
cgccaagcgt gtttgaagag cgggaacgtc cacattgcca acctgtgcaa agtggtcgcc    3000
ccggcaccca gcaggtcgag acccgagccc gtggtcgttt gcctccgtgg caagtccggt    3060
cagggcaaga gtttccttgc aaacgtgctc gcacaagcaa tctctaccca tttcactggc    3120
aggaccgatt cagtttggta ctgcccgcct gaccctgacc acttcgacgg ttacaaccaa    3180
cagactgtcg ttgtgatgga cgatttgggc cagaaccccg acggcaaaga cttcaagtac    3240
ttcgcccaaa tggtttcaac aacggggttc atcccgccca tggcatcgct tgaggataaa    3300 ggcaaacccct tcaacagtaa ggtcatcata gcaaccacca acctgtactc gggcttcacc    3360
ccgaggacta tggtgtgccc tgatgccctg aaccggaggt ttcactttga catcgacgtg    3420
agcgccaagg acgggtacaa aattaacaac aaattggaca tcatcaaagc acttgaagat    3480
actcacacca acccagtggc aatgtttcag tacgactgtg cccttctcaa cggcatggct    3540
gttgaaatga agagaatgca acaagatatg ttcaagcctc aaccacccct tcagaacgtg    3600
taccaactgg ttcaagaggt gattgagcgg gtggagctcc acgagaaggt gtcgagccac    3660
ccgattttca aacagatctc aattccttcc caaaaatccg tgttgtactt cctcattgag    3720
```

```
aaaggacagc acgaggcagc aattgaattc tttgagggca tggtgcacga ctccatcaag    3780
gaggagctcc ggccgctcat ccaacaaacc tcatttgtga aacgcgcttt taagcgcctg    3840
aaggaaaact ttgagattgt tgccctatgt ctgaccctcc tggccaacat agtgatcatg    3900
atccgcgaaa ctcgcaagag acagaagatg gtggacgatg cagtgagtga gtacattgag    3960
agagcaaaca tcaccaccga cgacaagact cttgatgagg cggaaaagaa ccctctggaa    4020
accagcggtg ccagcaccgt cggcttcaga gagagacctc tcccaggcca aaaggcgcgt    4080
aatgacgaga actccgagcc cgcccagcct gctgaagagc aaccacaagc tgaaggaccc    4140
tacgctggcc cgatggagag accagttaaa gttaaagtga agcaaaagc cccggtcgtt     4200 aaggaaggac cttacgaggg accggtgaag aagcctgttg ctttgaaagt gaaagctaag    4260
aacttgatcg tcactgagag tggtgcccca ccgaccgact tgcaaaagtt ggtcatgggc    4320
aacaccaagc ccgttgagct catccttgac gggaagacgg tagccatttg ctgtgctact    4380
ggagttttcg gcactgctta cctcgtgcct cgtcatcttt tcgcagaaaa gtacgacaag    4440
atcatgttgg acggcagagc catgacagat agtgactaca gagtgtttga gtttgagatt    4500
aaagtaaaag acaggacat gctctcagac gctgcgctca ggggccggcc aatccagtcc     4560
ggcgaccggc tcgcagaacc aatctggcaa cactggcagc ataattaaca actactacat    4620
gcagcaatac cagaactcca tggacacaca gttgggagac aatgccatca gtggaggctc    4680
caacgagggc tccacggaca caacttcaac acacacaacc aacactcaaa acaatgactg    4740
gttctcgaag ctcgccagtt cagcttttac cggtctgttc ggtgcactgc tcgccgacaa    4800
gaagacagag gaaacgacac ttcttgagga ccgcatcctc accacccgca acgggcacac    4860
cacctcgacg acccaatcga gtgtgggtgt cacacacggg tactccacag aggaggacca    4920
cgttgctggg cccaacacat cgggcctgga cgcgagtg gtgcaggcag agagattcta     4980
caaaaagtac ttgtttgact ggacaacgga caaggcattt ggacacctgg aaaagctgga    5040
gctcccgtcc gaccaccacg gtgtctttgg acacttggtg gactcgtacg cctatatgag    5100
aaatggctgg gatgttgagg tgtccgctgt tggcaaccag ttcaacggcg ggtgcctcct    5160
ggtggccatg gtacctgaat ggaaggaatt tgacacacgg gagaaatacc aactcaccct    5220
tttcccgcac cagtttatta gccccagaac taacatgact gcccacatca cggtcccccta   5280 ccttggtgtg aacaggtatg atcagtacaa gaagcataag ccctggacat tggttgtcat    5340
ggtcgtgtcg ccacttacgg tcaacaacac tagtgcggca caaatcaagg tctacgccaa    5400
catagctccg acctatgttc acgtggccgg tgaactcccc tcgaaagagg ggattttccc    5460
ggttgcatgt gcggacggtt acggaggatt ggtgacgaca gacccgaaga cagctgaccc    5520
tgcttatggc aaggtgtaca acccgcctag gactaactac cctgggcgct tcaccaacct    5580
gttggacgtg gccgaagcgt gtcccactt cctctgcttt gacgacggga aaccgtacgt     5640
caccacgcgg acgatgaca cccgactttt ggccaagttt gacctttccc ttgccgcaaa     5700
acatatgtcc aacacatacc tgtcagggat tgctcagtac tacacacagt actctggcac    5760
catcaatttg catttcatgt tcacaggttc cactgattca aaggcccgat acatggtggc    5820
ctacatccca cctggggtgg agacaccacc ggacacacct gaaagggctg cccactgcat    5880
tcacgctgaa tgggacactg gactaaactc caaattcact ttctcaatcc cgtacgtatc    5940
cgccgcggat tacgcgtaca cagcgtctga cacggcagaa acaatcaacg tacagggatg    6000
ggtctgcatc taccaaatta cacacgggaa ggctgaaaat gacaccttgg tcgtgtcggt    6060
tagcgccggc aaagactttg agttgcgcct cccgattgac cccgccagc agaccaccgc     6120
```

```
taccggggaa tcagcagacc cggtcaccac caccgtggag aactacggcg gtgagacaca    6180
aatccagaga cgtcaccaca cggacattgg tttcatcatg gacagatttg tgaagatcca    6240
aagcttgagc ccaacacatg tcattgacct catgcagact caccaacacg gtctggtggg    6300
tgccttgctg cgtgcagcca cgtactactt ttctgacctg gaaattgttg tacggcacga    6360
aggcaatctg acctgggtgc ccaacggcgc ccctgaatca gccctgttga acaccagcaa    6420
ccccactgcc tacaacaagg caccattcac gagactcgct ctccctaca ctgcgccgca     6480 ccgtgtgctg gcaacagtgt acaacgggac gagtaagtat gctgtgggtg gttcaggcag    6540
aagaggcgac atggggtctc tcgcggcgcg agtcgtgaaa cagcttcctg cttcatttaa    6600
ctacggtgca atcaaggccg acgccatcca cgaacttctc gtgcgcatga acgggccga    6660 gctctactgc cccagaccgc tgttggcaat agaggtgtct tcgcaagaca ggcacaagca    6720
aaagatcatt gcaccagcaa agcagcttct gaattttgac ctgcttaagc tagccggaga    6780
cgttgagtcc aaccctgggc ccttcttctt ctccgacgtt aggtcaaact tttccaagct    6840
ggtagacaca atcaaccaga tgcaggaaga catgtccaca aagcacggac ctgactttaa    6900
ccggttggtg tccgcttttg aggagttggc cactggagtg aaagccatca ggaccggtct    6960
tgacgaggcc aagccctggt acaagcttat caagctcctg agccgcctgt cgtgcatggc    7020
cgctgtggca gcacggtcaa aggacccagt ccttgtggcc atcatgctgg ctgacaccgg    7080
tctcgagatt ctggacagca ccttcgtcgt gaagaagatc tccgactcgc tctccagtct    7140
cttccacgtg ccggccccg tcttcagttt cggagcccg attctgttag ccgggttggt     7200
caaggtcgcc tcgagtttct tccggtccac gcccgaagac cttgagagag cagagaaaca    7260
gctcaaagca cgtgacatca cgacatttt cgccattctc aagaacggcg agtggctggt    7320
caaattgatc cttgccatcc gcgactggat caaggcatgg atagcctcag aagaaaagtt    7380
tgtcaccacg acagacttgg tacctagcat ccttgaaaaa cagcaggacc tcaacgaccc    7440
aagcaagtac aaggaagcca aggagtggct cgacaacgcg cgccaagcgt gtttgaagag    7500
cgggaacgtc cacattgcca acctgtgcaa agtggtcgcc ccggcaccca gcaggtcgag    7560
acccgagccc gtggtcgttt gcctccgtgg caagtccggt cagggcaaga gtttccttgc    7620
aaacgtgctc gcacaagcaa tctctaccca tttcactggc aggaccgatt cagtttggta    7680
ctgcccgcct gaccctgacc acttcgacgg ttacaaccaa cagactgtcg ttgtgatgga    7740
cgatttgggc cagaaccccg acggcaaaga cttcaagtac ttcgcccaaa tggtttcaac    7800 aacgggttc atcccgccca tggcatcgct tgaggataaa ggcaaaccct tcaacagtaa     7860
ggtcatcata gcaaccacca acctgtactc gggcttcacc ccgaggacta tggtgtgccc    7920
tgatgccctg aacggaggt ttcactttga catcgacgtg agcgcaagg acgggtacaa       7980 aattaacaac aaattggaca tcatcaaagc acttgaagat actcacacca acccagtggc    8040
aatgtttcag tacgactgtg cccttctcaa cggcatggct gttgaaatga gagaatgca     8100 acaagatatg ttcaagcctc aaccacccct tcagaacgtg taccaactgg ttcaagaggt    8160
gattgagcgg gtggagctcc acgagaaggt gtcgagccac ccgattttca acagatctc     8220 aattccttcc caaaaatccg tgttgtactt cctcattgag aaaggacagc acgaggcagc    8280
aattgaattc tttgagggca tggtgcacga ctccatcaag gaggagctcc ggccgctcat    8340
ccaacaaacc tcatttgtga aacgcgcttt taagcgcctg aaggaaaaact ttgagattgt    8400 tgccctatgt ctgaccctcc tggccaacat agtgatcatg atccgcgaaa ctcgcaagag    8460
```

```
acagaagatg gtggacgatg cagtgagtga gtacattgag agagcaaaca tcaccaccga    8520
cgacaagact cttgatgagg cggaaaagaa ccctctggaa accagcggtg ccagcaccgt    8580
cggcttcaga gagagacctc tcccaggcca aaaggcgcgt aatgacgaga actccgagcc    8640
cgcccagcct gctgaagagc aaccacaagc tgaaggaccc tacgctggcc cgatggagag    8700
accagttaaa gttaaagtga agcaaaagc cccggtcgtt aaggaaggac cttacgaggg    8760
accggtgaag aagcctgttg cttttgaaagt gaaagctaag aacttgatcg tcactgagag    8820
tggtgcccca ccgaccgact tgcaaaagtt ggtcatgggc aacaccaagc ccgttgagct    8880
catccttgac gggaagacgg tagccatttg ctgtgctact ggagttttcg gcactgctta    8940
cctcgtgcct cgtcatcttt tcgcagaaaa gtacgacaag atcatgttgg acggcagagc    9000
catgacagat agtgactaca gagtgtttga gtttgagatt aaagtaaaag gacaggacat    9060
gctctcagac gctgcgctca tggtgctcca ccgtgggaat cgcgtgagag acatcacgaa    9120
acactttcgt gacacagcaa gaatgaagaa aggcaccccc gtcgttggtg tgatcaacaa    9180
cgccgatgtc gggagactga ttttctctgg tgaagcccct acctacaagg acattgtagt    9240
gtgcatggat ggagacacca tgcctgggct cttttgcctac aaagccgcaa ccaaggctgg    9300
ttattgcgga ggagccgtcc tcgctaagga cggggctgac acgttcatcg ttggcaccca    9360
ctccgctgga ggcaatggcg ttggatactg ctcttgcgtt tccaggtcca tgcttctcaa    9420
gatgaaggca cacgttgacc ccgaaccaca ccacgagggg ttgattgttg acaccagaga    9480
tgtggaagag cgcgttcacg tgatgcgcaa aaccaagctt gcacccaccg ttgcgtacgg    9540
tgtgttccgt cctgagttcg ggcctgccgc cttgtccaac aaggacccgc gcctgaacga    9600
cggtgttgtc ctcgacgaag tcatcttctc caaacacaag ggagacacaa agatgtctga    9660
ggaagacaaa gcgctgttcc gccgctgtgc tgctgactac gcgtcacgcc tgcacagcgt    9720
gttgggtacg gcaaatgccc cactgagcat ctacgaggca attaaaggcg ttgatggact    9780
cgacgcaatg gaaccagaca ccgcacccgg cctcccctgg gcactccagg ggaagcgccg    9840
tggcgcgctc atcgacttcg agaacggcac tgttggaccc gaagttgagg ctgccttgaa    9900
gctcatggag aaaagagaat acaagtttgc ttgccaaacc ttcctgaagg acgagattcg    9960
cccgatggag aaagtacgtg ccggtaagac tcgcattgtc gacgtcctac ctgttgaaca   10020
catcctctac accaggatga tgattggcag attttgtgca caaatgcact caaacaacgg   10080
accccaaatt ggctcggcgg tcggttgtaa ccctgatgtt gattggcaaa gatttggcac   10140
acacttcgcc caatacagaa acgtgtggga tgtggactat tcggccttcg atgctaacca   10200
ctgcagtgac gccatgaaca tcatgtttga ggaagtgttt cgcacagaat tcgggttcca   10260
cccaaacgct gagtggatcc tgaagactct cgtgaacacg aacacgcct atgagaacaa   10320
acgcatcact gttgaaggcg ggatgccatc tggttgttcc gcaacaagca tcatcaacac   10380
aattttgaac aacatctacg tgctctacgc ttttgcgtaga cactatgagg gagttgagct   10440
ggacacttac accatgatct cttacggaga cgatatcgtg gtggcaagtg attacgattt   10500
ggactttgag gctctcaagc cccacttcaa atcccttggt caaaccatca ctccagctga   10560
caaaagcgac aaaggttttg ttcttggtca ctccattact gatgtcactt tcctcaaaag   10620
acacttccac atggattatg gaactgggtt ttacaaacct gtgatggcct caaagaccct   10680
tgaggctatc ctctcctttg cacgccgtgg gaccatacag gagaagttga tctccgtggc   10740
aggactcgct gttcactctg gaccagacga gtaccggcgt ctcttcgagc cctttcaagg   10800
cctcttcgag attccaagct acagatcact ttacctgcgt tgggtgaacg ccgtgtgcgg   10860
``` cgacgca                                                                                           10867

<210> SEQ ID NO 16
<211> LENGTH: 2109
<212> TYPE: PRT
<213> ORGANISM: Artificial Sequence
<220> FEATURE:
<223> OTHER INFORMATION: Fusion protein: Foot and Mouth Disease Virus
      (FMDV) and Bovine Rhinovirus Type 2 (BRV2)

<400> SEQUENCE: 16

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr His Gly Tyr Ser Thr Glu Glu Asp His Val
        115                 120                 125

Ala Gly Pro Asn Thr Ser Gly Leu Glu Thr Arg Val Val Gln Ala Glu
    130                 135                 140

Arg Phe Tyr Lys Lys Tyr Leu Phe Asp Trp Thr Thr Asp Lys Ala Phe
145                 150                 155                 160

Gly His Leu Glu Lys Leu Glu Leu Pro Ser Asp His His Gly Val Phe
                165                 170                 175

Gly His Leu Val Asp Ser Tyr Ala Tyr Met Arg Asn Gly Trp Asp Val
            180                 185                 190

Glu Val Ser Ala Val Gly Asn Gln Phe Asn Gly Gly Cys Leu Leu Val
        195                 200                 205

Ala Met Val Pro Glu Trp Lys Glu Phe Asp Thr Arg Glu Lys Tyr Gln
    210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Lys His Lys Pro Trp Thr Leu Val Val Met Val Val Ser Pro Leu
            260                 265                 270

Thr Val Asn Asn Thr Ser Ala Ala Gln Ile Lys Val Tyr Ala Asn Ile
        275                 280                 285

Ala Pro Thr Tyr Val His Val Ala Gly Glu Leu Pro Ser Lys Glu Gly
    290                 295                 300

Ile Phe Pro Val Ala Cys Ala Asp Gly Tyr Gly Gly Leu Val Thr Thr
305                 310                 315                 320

Asp Pro Lys Thr Ala Asp Pro Ala Tyr Gly Lys Val Tyr Asn Pro Pro
                325                 330                 335

Arg Thr Asn Tyr Pro Gly Arg Phe Thr Asn Leu Leu Asp Val Ala Glu
            340                 345                 350

```
Ala Cys Pro Thr Phe Leu Cys Phe Asp Asp Gly Lys Pro Tyr Val Thr
        355                 360                 365

Thr Arg Thr Asp Asp Thr Arg Leu Leu Ala Lys Phe Asp Leu Ser Leu
370                 375                 380

Ala Ala Lys His Met Ser Asn Thr Tyr Leu Ser Gly Ile Ala Gln Tyr
385                 390                 395                 400

Tyr Thr Gln Tyr Ser Gly Thr Ile Asn Leu His Phe Met Phe Thr Gly
                405                 410                 415

Ser Thr Asp Ser Lys Ala Arg Tyr Met Val Ala Tyr Ile Pro Pro Gly
                420                 425                 430

Val Glu Thr Pro Pro Asp Thr Pro Glu Arg Ala Ala His Cys Ile His
        435                 440                 445

Ala Glu Trp Asp Thr Gly Leu Asn Ser Lys Phe Thr Phe Ser Ile Pro
450                 455                 460

Tyr Val Ser Ala Ala Asp Tyr Ala Tyr Thr Ala Ser Asp Thr Ala Glu
465                 470                 475                 480

Thr Ile Asn Val Gln Gly Trp Val Cys Ile Tyr Gln Ile Thr His Gly
                485                 490                 495

Lys Ala Glu Asn Asp Thr Leu Val Val Ser Val Ser Ala Gly Lys Asp
                500                 505                 510

Phe Glu Leu Arg Leu Pro Ile Asp Pro Arg Gln Gln Thr Thr Ala Thr
        515                 520                 525

Gly Glu Ser Ala Asp Pro Val Thr Thr Val Glu Asn Tyr Gly Gly
530                 535                 540

Glu Thr Gln Ile Gln Arg Arg His His Thr Asp Ile Gly Phe Ile Met
545                 550                 555                 560

Asp Arg Phe Val Lys Ile Gln Ser Leu Ser Pro Thr His Val Ile Asp
                565                 570                 575

Leu Met Gln Thr His Gln His Gly Leu Val Gly Ala Leu Leu Arg Ala
                580                 585                 590

Ala Thr Tyr Tyr Phe Ser Asp Leu Glu Ile Val Val Arg His Glu Gly
        595                 600                 605

Asn Leu Thr Trp Val Pro Asn Gly Ala Pro Glu Ser Ala Leu Leu Asn
610                 615                 620

Thr Ser Asn Pro Thr Ala Tyr Asn Lys Ala Pro Phe Thr Arg Leu Ala
625                 630                 635                 640

Leu Pro Tyr Thr Ala Pro His Arg Val Leu Ala Thr Val Tyr Asn Gly
                645                 650                 655

Thr Ser Lys Tyr Ala Val Gly Gly Ser Gly Arg Arg Gly Asp Met Gly
                660                 665                 670

Ser Leu Ala Ala Arg Val Val Lys Gln Leu Pro Ala Ser Phe Asn Tyr
            675                 680                 685

Gly Ala Ile Lys Ala Asp Ala Ile His Glu Leu Leu Val Arg Met Lys
        690                 695                 700

Arg Ala Glu Leu Tyr Cys Pro Arg Pro Leu Leu Ala Ile Glu Val Ser
705                 710                 715                 720

Ser Gln Asp Arg His Lys Gln Lys Ile Ile Ala Pro Ala Lys Gln Leu
            725                 730                 735

Leu Asn Phe Asp Leu Leu Lys Leu Ala Gly Asp Val Glu Ser Asn Pro
                740                 745                 750

Gly Pro Phe Phe Phe Ser Asp Val Arg Ser Asn Phe Ser Lys Leu Val
        755                 760                 765
```

-continued

```
Asp Thr Ile Asn Gln Met Gln Glu Asp Met Ser Thr Lys His Gly Pro
770                 775                 780

Asp Phe Asn Arg Leu Val Ser Ala Phe Glu Glu Leu Ala Thr Gly Val
785                 790                 795                 800

Lys Ala Ile Arg Thr Gly Leu Asp Glu Ala Lys Pro Trp Tyr Lys Leu
                805                 810                 815

Ile Lys Leu Leu Ser Arg Leu Ser Cys Met Ala Ala Val Ala Ala Arg
                820                 825                 830

Ser Lys Asp Pro Val Leu Val Ala Ile Met Leu Ala Asp Thr Gly Leu
                835                 840                 845

Glu Ile Leu Asp Ser Thr Phe Val Val Lys Lys Ile Ser Asp Ser Leu
850                 855                 860

Ser Ser Leu Phe His Val Pro Ala Pro Val Phe Ser Phe Gly Ala Pro
865                 870                 875                 880

Ile Leu Leu Ala Gly Leu Val Lys Val Ala Ser Ser Phe Phe Arg Ser
                885                 890                 895

Thr Pro Glu Asp Leu Glu Arg Ala Glu Lys Gln Leu Lys Ala Arg Asp
                900                 905                 910

Ile Asn Asp Ile Phe Ala Ile Leu Lys Asn Gly Glu Trp Leu Val Lys
                915                 920                 925

Leu Ile Leu Ala Ile Arg Asp Trp Ile Lys Ala Trp Ile Ala Ser Glu
930                 935                 940

Glu Lys Phe Val Thr Thr Asp Leu Val Pro Ser Ile Leu Glu Lys
945                 950                 955                 960

Gln Gln Asp Leu Asn Asp Pro Ser Lys Tyr Lys Glu Ala Lys Glu Trp
                965                 970                 975

Leu Asp Asn Ala Arg Gln Ala Cys Leu Lys Ser Gly Asn Val His Ile
                980                 985                 990

Ala Asn Leu Cys Lys Val Val Ala  Pro Ala Pro Ser Arg  Ser Arg Pro
                995                1000                1005

Glu Pro  Val Val Val Cys  Leu Arg Gly Lys Ser Gly  Gln Gly Lys
    1010                1015                1020

Ser Phe  Leu Ala Asn Val Leu  Ala Gln Ala Ile Ser  Thr His Phe
    1025                1030                1035

Thr Gly  Arg Thr Asp Ser Val  Trp Tyr Cys Pro Pro  Asp Pro Asp
    1040                1045                1050

His Phe  Asp Gly Tyr Asn Gln  Gln Thr Val Val  Met Asp Asp
    1055                1060                1065

Leu Gly  Gln Asn Pro Asp Gly  Lys Asp Phe Lys Tyr  Phe Ala Gln
    1070                1075                1080

Met Val  Ser Thr Thr Gly Phe  Ile Pro Pro Met Ala  Ser Leu Glu
    1085                1090                1095

Asp Lys  Gly Lys Pro Phe Asn  Ser Lys Val Ile  Ala Thr Thr
    1100                1105                1110

Asn Leu  Tyr Ser Gly Phe Thr  Pro Arg Thr Met Val  Cys Pro Asp
    1115                1120                1125

Ala Leu  Asn Arg Arg Phe His  Phe Asp Ile Asp Val  Ser Ala Lys
    1130                1135                1140

Asp Gly  Tyr Lys Ile Asn Asn  Lys Leu Asp Ile Ile  Lys Ala Leu
    1145                1150                1155

Glu Asp  Thr His Thr Asn Pro  Val Ala Met Phe Gln  Tyr Asp Cys
    1160                1165                1170

Ala Leu  Leu Asn Gly Met Ala  Val Glu Met Lys Arg  Met Gln Gln
```

-continued

```
            1175                1180                1185
Asp Met Phe Lys Pro Gln Pro Pro Leu Gln Asn Val Tyr Gln Leu
        1190                1195                1200
Val Gln Glu Val Ile Glu Arg Val Glu Leu His Glu Lys Val Ser
        1205                1210                1215
Ser His Pro Ile Phe Lys Gln Ile Ser Ile Pro Ser Gln Lys Ser
        1220                1225                1230
Val Leu Tyr Phe Leu Ile Glu Lys Gly Gln His Glu Ala Ala Ile
        1235                1240                1245
Glu Phe Phe Glu Gly Met Val His Asp Ser Ile Lys Glu Glu Leu
        1250                1255                1260
Arg Pro Leu Ile Gln Gln Thr Ser Phe Val Lys Arg Ala Phe Lys
        1265                1270                1275
Arg Leu Lys Glu Asn Phe Glu Ile Val Ala Leu Cys Leu Thr Leu
        1280                1285                1290
Leu Ala Asn Ile Val Ile Met Ile Arg Glu Thr Arg Lys Arg Gln
        1295                1300                1305
Lys Met Val Asp Asp Ala Val Ser Glu Tyr Ile Glu Arg Ala Asn
        1310                1315                1320
Ile Thr Thr Asp Asp Lys Thr Leu Asp Glu Ala Glu Lys Asn Pro
        1325                1330                1335
Leu Glu Thr Ser Gly Ala Ser Thr Val Gly Phe Arg Glu Arg Pro
        1340                1345                1350
Leu Pro Gly Gln Lys Ala Arg Asn Asp Glu Asn Ser Glu Pro Ala
        1355                1360                1365
Gln Pro Ala Glu Glu Gln Pro Gln Ala Glu Gly Pro Tyr Ala Gly
        1370                1375                1380
Pro Met Glu Arg Pro Val Lys Val Lys Val Lys Ala Lys Ala Pro
        1385                1390                1395
Val Val Lys Glu Gly Pro Tyr Glu Gly Pro Val Lys Lys Pro Val
        1400                1405                1410
Ala Leu Lys Val Lys Ala Lys Asn Leu Ile Val Thr Glu Ser Gly
        1415                1420                1425
Ala Pro Pro Thr Asp Leu Gln Lys Leu Val Met Gly Asn Thr Lys
        1430                1435                1440
Pro Val Glu Leu Ile Leu Asp Gly Lys Thr Val Ala Ile Cys Cys
        1445                1450                1455
Ala Thr Gly Val Phe Gly Thr Ala Tyr Leu Val Pro Arg His Leu
        1460                1465                1470
Phe Ala Glu Lys Tyr Asp Lys Ile Met Leu Asp Gly Arg Ala Met
        1475                1480                1485
Thr Asp Ser Asp Tyr Arg Val Phe Glu Phe Glu Ile Lys Val Lys
        1490                1495                1500
Gly Gln Asp Met Leu Ser Asp Ala Ala Leu Met Val Leu His Arg
        1505                1510                1515
Gly Asn Arg Val Arg Asp Ile Thr Lys His Phe Arg Asp Thr Ala
        1520                1525                1530
Arg Met Lys Lys Gly Thr Pro Val Val Gly Val Ile Asn Asn Ala
        1535                1540                1545
Asp Val Gly Arg Leu Ile Phe Ser Gly Glu Ala Leu Thr Tyr Lys
        1550                1555                1560
Asp Ile Val Val Cys Met Asp Gly Asp Thr Met Pro Gly Leu Phe
        1565                1570                1575
```

```
Ala Tyr Lys Ala Ala Thr Lys Ala Gly Tyr Cys Gly Gly Ala Val
    1580            1585            1590

Leu Ala Lys Asp Gly Ala Asp Thr Phe Ile Val Gly Thr His Ser
    1595            1600            1605

Ala Gly Gly Asn Gly Val Gly Tyr Cys Ser Cys Val Ser Arg Ser
    1610            1615            1620

Met Leu Leu Lys Met Lys Ala His Val Asp Pro Glu Pro His His
    1625            1630            1635

Glu Gly Leu Ile Val Asp Thr Arg Asp Val Glu Glu Arg Val His
    1640            1645            1650

Val Met Arg Lys Thr Lys Leu Ala Pro Thr Val Ala Tyr Gly Val
    1655            1660            1665

Phe Arg Pro Glu Phe Gly Pro Ala Ala Leu Ser Asn Lys Asp Pro
    1670            1675            1680

Arg Leu Asn Asp Gly Val Val Leu Asp Glu Val Ile Phe Ser Lys
    1685            1690            1695

His Lys Gly Asp Thr Lys Met Ser Glu Glu Asp Lys Ala Leu Phe
    1700            1705            1710

Arg Arg Cys Ala Ala Asp Tyr Ala Ser Arg Leu His Ser Val Leu
    1715            1720            1725

Gly Thr Ala Asn Ala Pro Leu Ser Ile Tyr Glu Ala Ile Lys Gly
    1730            1735            1740

Val Asp Gly Leu Asp Ala Met Glu Pro Asp Thr Ala Pro Gly Leu
    1745            1750            1755

Pro Trp Ala Leu Gln Gly Lys Arg Arg Gly Ala Leu Ile Asp Phe
    1760            1765            1770

Glu Asn Gly Thr Val Gly Pro Glu Val Glu Ala Ala Leu Lys Leu
    1775            1780            1785

Met Glu Lys Arg Glu Tyr Lys Phe Ala Cys Gln Thr Phe Leu Lys
    1790            1795            1800

Asp Glu Ile Arg Pro Met Glu Lys Val Arg Ala Gly Lys Thr Arg
    1805            1810            1815

Ile Val Asp Val Leu Pro Val Glu His Ile Leu Tyr Thr Arg Met
    1820            1825            1830

Met Ile Gly Arg Phe Cys Ala Gln Met His Ser Asn Asn Gly Pro
    1835            1840            1845

Gln Ile Gly Ser Ala Val Gly Cys Asn Pro Asp Val Asp Trp Gln
    1850            1855            1860

Arg Phe Gly Thr His Phe Ala Gln Tyr Arg Asn Val Trp Asp Val
    1865            1870            1875

Asp Tyr Ser Ala Phe Asp Ala Asn His Cys Ser Asp Ala Met Asn
    1880            1885            1890

Ile Met Phe Glu Glu Val Phe Arg Thr Glu Phe Gly Phe His Pro
    1895            1900            1905

Asn Ala Glu Trp Ile Leu Lys Thr Leu Val Asn Thr Glu His Ala
    1910            1915            1920

Tyr Glu Asn Lys Arg Ile Thr Val Glu Gly Gly Met Pro Ser Gly
    1925            1930            1935

Cys Ser Ala Thr Ser Ile Ile Asn Thr Ile Leu Asn Asn Ile Tyr
    1940            1945            1950

Val Leu Tyr Ala Leu Arg Arg His Tyr Glu Gly Val Glu Leu Asp
    1955            1960            1965
```

```
Thr Tyr Thr Met Ile Ser Tyr Gly Asp Asp Ile Val Val Ala Ser
    1970            1975            1980

Asp Tyr Asp Leu Asp Phe Glu Ala Leu Lys Pro His Phe Lys Ser
    1985            1990            1995

Leu Gly Gln Thr Ile Thr Pro Ala Asp Lys Ser Asp Lys Gly Phe
    2000            2005            2010

Val Leu Gly His Ser Ile Thr Asp Val Thr Phe Leu Lys Arg His
    2015            2020            2025

Phe His Met Asp Tyr Gly Thr Gly Phe Tyr Lys Pro Val Met Ala
    2030            2035            2040

Ser Lys Thr Leu Glu Ala Ile Leu Ser Phe Ala Arg Arg Gly Thr
    2045            2050            2055

Ile Gln Glu Lys Leu Ile Ser Val Ala Gly Leu Ala Val His Ser
    2060            2065            2070

Gly Pro Asp Glu Tyr Arg Arg Leu Phe Glu Pro Phe Gln Gly Leu
    2075            2080            2085

Phe Glu Ile Pro Ser Tyr Arg Ser Leu Tyr Leu Arg Trp Val Asn
    2090            2095            2100

Ala Val Cys Gly Asp Ala
    2105

<210> SEQ ID NO 17
<211> LENGTH: 6327
<212> TYPE: DNA
<213> ORGANISM: Artificial Sequence
<220> FEATURE:
<223> OTHER INFORMATION: Fusion nucleotide:  Foot and Mouth Disease
      Virus (FMDV) and Bovine Rhinovirus Type 2 (BRV2)

<400> SEQUENCE: 17
ggggccggcc aatccagtcc ggcgaccggc tcgcagaacc aatctggcaa cactggcagc      60
ataattaaca actactacat gcagcaatac cagaactcca tggacacaca gttgggagac     120
aatgccatca gtggaggctc caacgagggc tccacgacca caacttcaac acacacaacc     180
aacactcaaa acaatgactg gttctcgaag ctcgccagtt cagcttttac cggtctgttc     240
ggtgcactgc tcgccgacaa gagacagag gaaacgacac ttcttgagga ccgcatcctc     300
accacccgca acgggcacac cacctcgacg acccaatcga gtgtgggtgt cacacacggg     360
tactccacag aggaggacca cgttgctggg cccaacacat cgggcctgga cgcgagtg      420 gtgcaggcag agagattcta caaaaagtac ttgtttgact ggacaacgga caaggcattt     480
ggacacctgg aaaagctgga gctcccgtcc gaccaccacg tgtctttgg acacttggtg      540 gactcgtacg cctatatgag aaatggctgg gatgttgagg tgtccgctgt tggcaaccag     600
ttcaacggcg ggtgcctcct ggtggccatg gtacctgaat ggaaggaatt tgacacacgg     660
gagaaatacc aactcacccct ttttcccgcac cagtttatta gccccagaac taacatgact     720
gcccacatca cggtccccta ccttggtgtg aacaggtatg atcagtacaa gaagcataag     780
ccctggacat tggttgtcat ggtcgtgtcg ccacttacgg tcaacaacac tagtgcggca     840
caaatcaagg tctacgccaa catagctccg acctatgttc acgtggccgg tgaactcccc     900
tcgaaagagg ggatttttccc ggttgcatgt gcggacggtt acgaggatt ggtgacgaca     960 gacccgaaga cagctgaccc tgcttatggc aaggtgtaca accggcctag gactaactac    1020
cctgggcgct tcaccaacct gttggacgtg gccgaagcgt gtcccacttt cctctgcttt    1080
gacgacggga aaccgtacgt caccacgcgg acggatgaca cccgacttt ggccaagttt    1140
```

```
gacctttccc ttgccgcaaa acatatgtcc aacacatacc tgtcagggat tgctcagtac    1200
tacacacagt actctggcac catcaatttg catttcatgt tcacaggttc cactgattca    1260
aaggcccgat acatggtggc ctacatccca cctggggtgg agacaccacc ggacacacct    1320
gaaagggctg cccactgcat tcacgctgaa tgggacactg gactaaactc caaattcact    1380
ttctcaatcc cgtacgtatc cgccgcggat tacgcgtaca cagcgtctga cacggcagaa    1440
acaatcaacg tacagggatg ggtctgcatc taccaaatta cacacgggaa ggctgaaaat    1500
gacaccttgg tcgtgtcggt tagcgccggc aaagactttg agttgcgcct cccgattgac    1560
ccccgccagc agaccaccgc taccggggaa tcagcagacc cggtcaccac caccgtggag    1620
aactacggcg gtgagacaca atccagaga cgtcaccaca cggacattgg tttcatcatg    1680
gacagatttg tgaagatcca aagcttgagc ccaacacatg tcattgacct catgcagact    1740
caccaacacg gtctggtggg tgccttgctg cgtgcagcca cgtactactt ttctgacctg    1800
gaaattgttg tacggcacga aggcaatctg acctgggtgc ccaacggcgc ccctgaatca    1860
gccctgttga acaccagcaa ccccactgcc tacaacaagg caccattcac gagactcgct    1920
ctcccctaca ctgcgccgca ccgtgtgctg gcaacagtgt acaacgggac gagtaagtat    1980
gctgtgggtg gttcaggcag aagaggcgac atggggtctc tcgcggcgcg agtcgtgaaa    2040
cagcttcctg cttcatttaa ctacggtgca atcaaggccg acgccatcca cgaacttctc    2100
gtgcgcatga acgggccga gctctactgc cccagaccgc tgttggcaat agaggtgtct    2160
tcgcaagaca ggcacaagca aaagatcatt gcaccagcaa agcagcttct gaattttgac    2220
ctgcttaagc tagccggaga cgttgagtcc aaccctgggc ccttcttctt ctccgacgtt    2280 aggtcaaaact tttccaagct ggtagacaca atcaaccaga tgcaggaaga catgtccaca    2340
aagcacggac ctgactttaa ccggttggtg tccgcttttg aggagttggc cactggagtg    2400
aaagccatca ggaccggtct tgacgaggcc aagccctggt acaagcttat caagctcctg    2460
agccgcctgt cgtgcatggc cgctgtggca gcacggtcaa aggacccagt ccttgtggcc    2520
atcatgctgg ctgacaccgg tctcgagatt ctggacagca ccttcgtcgt gaagaagatc    2580
tccgactcgc tctccagtct cttccacgtg ccggcccccg tcttcagttt cggagccccg    2640
attctgttag ccgggttggt caaggtcgcc tcgagtttct tccggtccac gcccgaagac    2700
cttgagagag cagagaaaca gctcaaagca cgtgacatca cgacattttt cgccattctc    2760
aagaacggcg agtggctggt caaattgatc cttgccatcc gcgactggat caaggcatgg    2820
atagcctcag aagaaaagtt tgtcaccacg acagacttgg tacctagcat ccttgaaaaa    2880
cagcaggacc tcaacgaccc aagcaagtac aaggaagcca aggagtggct cgacaacgcg    2940
cgccaagcgt gtttgaagag cgggaacgtc cacattgcca acctgtgcaa agtggtcgcc    3000
ccggcaccca gcaggtcgag acccgagccc gtggtcgttt gcctccgtgg caagtccggt    3060
cagggcaaga gtttccttgc aaacgtgctc gcacaagcaa tctctaccca tttcactggc    3120
aggaccgatt cagtttggta ctgcccgcct gaccctgacc acttcgacgg ttacaaccaa    3180
cagactgtcg ttgtgatgga cgatttgggc cagaaccccg acggcaaaga cttcaagtac    3240
ttcgcccaaa tggtttcaac aacgggttc atcccgccca tggcatcgct tgaggataaa    3300
ggcaaaccct tcaacagtaa ggtcatcata gcaaccacca acctgtactc gggcttcacc    3360
ccgaggacta tggtgtgccc tgatgccctg aaccggaggt ttcactttga catcgacgtg    3420
agcgccaagg acgggtacaa aattaacaac aaattggaca tcatcaaagc acttgaagat    3480
actcacacca acccagtggc aatgtttcag tacgactgtg cccttctcaa cggcatggct    3540
```

```
gttgaaatga agagaatgca acaagatatg ttcaagcctc aaccacccct tcagaacgtg    3600
taccaactgg ttcaagaggt gattgagcgg gtggagctcc acgagaaggt gtcgagccac    3660
ccgattttca aacagatctc aattccttcc caaaaatccg tgttgtactt cctcattgag    3720
aaaggacagc acgaggcagc aattgaattc tttgagggca tggtgcacga ctccatcaag    3780
gaggagctcc ggccgctcat ccaacaaacc tcatttgtga aacgcgcttt taagcgcctg    3840
aaggaaaact ttgagattgt tgccctatgt ctgaccctcc tggccaacat agtgatcatg    3900
atccgcgaaa ctcgcaagag acagaagatg gtggacgatg cagtgagtga gtacattgag    3960
agagcaaaca tcaccaccga cgacaagact cttgatgagg cggaaaagaa ccctctggaa    4020
accagcggtg ccagcaccgt cggcttcaga gagagacctc tcccaggcca aaaggcgcgt    4080
aatgacgaga actccgagcc cgcccagcct gctgaagagc aaccacaagc tgaaggaccc    4140
tacgctggcc cgatggagag acagaaacca ctgaaagtga agcaaaagc cccggtcgtt     4200 aaggaaggac cttacgaggg accggtgaag aagcctgttg ctttgaaagt gaaagctaag    4260
aacttgatcg tcactgagag tggtgccccc ccgaccgact tgcaaaagtt ggtcatgggc    4320
aacaccaagc ccgttgagct catccttgac gggaagacgg tagccatttg ctgtgctact    4380
ggagttttcg gcactgctta cctcgtgcct cgtcatcttt tcgcagaaaa gtacgacaag    4440
atcatgttgg acggcagagc catgacagat agtgactaca gagtgtttga gtttgagatt    4500
aaagtaaaag gacaggacat gctctcagac gctgcgctca tggtgctcca ccgtgggaat    4560
cgcgtgagag acatcacgaa acactttcgt gacacagcaa gaatgaagaa aggcaccccc    4620
gtcgttggtg tgatcaacaa cgccgatgtc gggagactga ttttctctgg tgaagccctt    4680
acctacaagg acattgtagt gtgcatggat ggagacacca tgcctgggct ctttgcctac    4740
aaagccgcaa ccaaggctgg ttattgcgga ggagccgtcc tcgctaagga cggggctgac    4800
acgttcatcg ttggcaccca ctccgctgga ggcaatggcg ttggatactg ctcttgcgtt    4860
tccaggtcca tgcttctcaa gatgaaggca cacgttgacc ccgaaccaca ccacgagggg    4920
ttgattgttg acaccagaga tgtggaagag cgcgttcacg tgatgcgcaa aaccaagctt    4980
gcacccaccg ttgcgtacgg tgtgttccgt cctgagttcg ggcctgccgc cttgtccaac    5040
aaggacccgc gcctaacgac cggtgttgtc ctcgacgaag tcatcttctc caaacacaag    5100
ggagacacaa agatgtctga ggaagacaaa gcgctgttcc gccgctgtgc tgctgactac    5160
gcgtcacgcc tgcacagcgt gttgggtacg gcaaatgccc cactgagcat ctacgaggca    5220
attaaaggcg ttgatggact cgacgcaatg gaaccagaca ccgcacccgg cctcccctgg    5280
gcactccagg ggaagcgccg tggcgcgctc atcgacttcg agaacggcac tgttggaccc    5340
gaagttgagg ctgccttgaa gctcatggag aaaagagaat acaagtttgc ttgccaaacc    5400
ttcctgaagg acgagattcg cccgatggag aaagtacgtg ccggtaagac tcgcattgtc    5460
gacgtcctac tgttgaaca catcctctac accaggatga tgattggcag attttgtgca     5520
caaatgcact caaacaacgg accccaaatt ggctcggcgg tcggttgtaa ccctgatgtt    5580
gattggcaaa gatttggcac acacttcgcc caatacagaa acgtgtggga tgtggactat    5640
tcggccttcg atgctaacca ctgcagtgac gccatgaaca tcatgtttga ggaagtgttt    5700
cgcacagaat tcgggttcca cccaaacgct gagtggatcc tgaagactct cgtgaacacg    5760
gaacacgcct atgagaacaa acgcatcact gttgaaggcg ggatgccatc tggttgttcc    5820
gcaacaagca tcatcaacac aatttttgaac aacatctacg tgctctacgc tttgcgtaga    5880
```

```
cactatgagg gagttgagct ggacacttac accatgatct cttacggaga cgatatcgtg    5940
gtggcaagtg attacgattt ggactttgag gctctcaagc cccacttcaa atcccttggt    6000
caaaccatca ctccagctga caaaagcgac aaaggttttg ttcttggtca ctccattact    6060
gatgtcactt tcctcaaaag acacttccac atggattatg gaactgggtt ttacaaacct    6120
gtgatggcct caaagaccct tgaggctatc ctctcctttg cacgccgtgg gaccatacag    6180
gagaagttga tctccgtggc aggactcgct gttcactctg gaccagacga gtaccggcgt    6240
ctcttcgagc cctttcaagg cctcttcgag attccaagct acagatcact ttacctgcgt    6300
tgggtgaacg ccgtgtgcgg cgacgca                                        6327
```

<210> SEQ ID NO 18
<211> LENGTH: 2109
<212> TYPE: PRT
<213> ORGANISM: Artificial Sequence
<220> FEATURE:
<223> OTHER INFORMATION: Fusion protein: Foot and Mouth Disease Virus
      (FMDV) and Bovine Rhinovirus Type 2 (BRV2)

<400> SEQUENCE: 18

```
Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr His Gly Tyr Ser Thr Glu Glu Asp His Val
        115                 120                 125

Ala Gly Pro Asn Thr Ser Gly Leu Glu Thr Arg Val Val Gln Ala Glu
    130                 135                 140

Arg Phe Tyr Lys Lys Tyr Leu Phe Asp Trp Thr Thr Asp Lys Ala Phe
145                 150                 155                 160

Gly His Leu Glu Lys Leu Glu Leu Pro Ser Asp His His Gly Val Phe
                165                 170                 175

Gly His Leu Val Asp Ser Tyr Ala Tyr Met Arg Asn Gly Trp Asp Val
            180                 185                 190

Glu Val Ser Ala Val Gly Asn Gln Phe Asn Gly Gly Cys Leu Leu Val
        195                 200                 205

Ala Met Val Pro Glu Trp Lys Glu Phe Asp Thr Arg Glu Lys Tyr Gln
    210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Lys His Lys Pro Trp Thr Leu Val Val Met Val Val Ser Pro Leu
            260                 265                 270

Thr Val Asn Asn Thr Ser Ala Ala Gln Ile Lys Val Tyr Ala Asn Ile
```

```
            275                 280                 285
Ala Pro Thr Tyr Val His Val Ala Gly Glu Leu Pro Ser Lys Glu Gly
290                 295                 300
Ile Phe Pro Val Ala Cys Ala Asp Gly Tyr Gly Gly Leu Val Thr Thr
305                 310                 315                 320
Asp Pro Lys Thr Ala Asp Pro Ala Tyr Gly Lys Val Tyr Asn Pro Pro
                325                 330                 335
Arg Thr Asn Tyr Pro Gly Arg Phe Thr Asn Leu Leu Asp Val Ala Glu
                340                 345                 350
Ala Cys Pro Thr Phe Leu Cys Phe Asp Asp Gly Lys Pro Tyr Val Thr
                355                 360                 365
Thr Arg Thr Asp Asp Thr Arg Leu Leu Ala Lys Phe Asp Leu Ser Leu
                370                 375                 380
Ala Ala Lys His Met Ser Asn Thr Tyr Leu Ser Gly Ile Ala Gln Tyr
385                 390                 395                 400
Tyr Thr Gln Tyr Ser Gly Thr Ile Asn Leu His Phe Met Phe Thr Gly
                405                 410                 415
Ser Thr Asp Ser Lys Ala Arg Tyr Met Val Ala Tyr Ile Pro Pro Gly
                420                 425                 430
Val Glu Thr Pro Pro Asp Thr Pro Glu Arg Ala Ala His Cys Ile His
                435                 440                 445
Ala Glu Trp Asp Thr Gly Leu Asn Ser Lys Phe Thr Phe Ser Ile Pro
450                 455                 460
Tyr Val Ser Ala Ala Asp Tyr Ala Tyr Thr Ala Ser Asp Thr Ala Glu
465                 470                 475                 480
Thr Ile Asn Val Gln Gly Trp Val Cys Ile Tyr Gln Ile Thr His Gly
                485                 490                 495
Lys Ala Glu Asn Asp Thr Leu Val Val Ser Val Ser Ala Gly Lys Asp
                500                 505                 510
Phe Glu Leu Arg Leu Pro Ile Asp Pro Arg Gln Gln Thr Thr Ala Thr
                515                 520                 525
Gly Glu Ser Ala Asp Pro Val Thr Thr Thr Val Glu Asn Tyr Gly Gly
                530                 535                 540
Glu Thr Gln Ile Gln Arg Arg His His Thr Asp Ile Gly Phe Ile Met
545                 550                 555                 560
Asp Arg Phe Val Lys Ile Gln Ser Leu Ser Pro Thr His Val Ile Asp
                565                 570                 575
Leu Met Gln Thr His Gln His Gly Leu Val Gly Ala Leu Leu Arg Ala
                580                 585                 590
Ala Thr Tyr Tyr Phe Ser Asp Leu Glu Ile Val Val Arg His Glu Gly
                595                 600                 605
Asn Leu Thr Trp Val Pro Asn Gly Ala Pro Glu Ser Ala Leu Leu Asn
                610                 615                 620
Thr Ser Asn Pro Thr Ala Tyr Asn Lys Ala Pro Phe Thr Arg Leu Ala
625                 630                 635                 640
Leu Pro Tyr Thr Ala Pro His Arg Val Leu Ala Thr Val Tyr Asn Gly
                645                 650                 655
Thr Ser Lys Tyr Ala Val Gly Gly Ser Gly Arg Arg Gly Asp Met Gly
                660                 665                 670
Ser Leu Ala Ala Arg Val Val Lys Gln Leu Pro Ala Ser Phe Asn Tyr
                675                 680                 685
Gly Ala Ile Lys Ala Asp Ala Ile His Glu Leu Leu Val Arg Met Lys
                690                 695                 700
```

```
Arg Ala Glu Leu Tyr Cys Pro Arg Pro Leu Leu Ala Ile Glu Val Ser
705                 710                 715                 720

Ser Gln Asp Arg His Lys Gln Lys Ile Ile Ala Pro Ala Lys Gln Leu
            725                 730                 735

Leu Asn Phe Asp Leu Leu Lys Leu Ala Gly Asp Val Glu Ser Asn Pro
        740                 745                 750

Gly Pro Phe Phe Phe Ser Asp Val Arg Ser Asn Phe Ser Lys Leu Val
        755                 760                 765

Asp Thr Ile Asn Gln Met Gln Glu Asp Met Ser Thr Lys His Gly Pro
770                 775                 780

Asp Phe Asn Arg Leu Val Ser Ala Phe Glu Glu Leu Ala Thr Gly Val
785                 790                 795                 800

Lys Ala Ile Arg Thr Gly Leu Asp Glu Ala Lys Pro Trp Tyr Lys Leu
            805                 810                 815

Ile Lys Leu Leu Ser Arg Leu Ser Cys Met Ala Val Ala Ala Ala Arg
        820                 825                 830

Ser Lys Asp Pro Val Leu Val Ala Ile Met Leu Ala Asp Thr Gly Leu
    835                 840                 845

Glu Ile Leu Asp Ser Thr Phe Val Val Lys Lys Ile Ser Asp Ser Leu
850                 855                 860

Ser Ser Leu Phe His Val Pro Ala Pro Val Phe Ser Phe Gly Ala Pro
865                 870                 875                 880

Ile Leu Leu Ala Gly Leu Val Lys Val Ala Ser Ser Phe Phe Arg Ser
            885                 890                 895

Thr Pro Glu Asp Leu Glu Arg Ala Glu Lys Gln Leu Lys Ala Arg Asp
        900                 905                 910

Ile Asn Asp Ile Phe Ala Ile Leu Lys Asn Gly Glu Trp Leu Val Lys
    915                 920                 925

Leu Ile Leu Ala Ile Arg Asp Trp Ile Lys Ala Trp Ile Ala Ser Glu
930                 935                 940

Glu Lys Phe Val Thr Thr Thr Asp Leu Val Pro Ser Ile Leu Glu Lys
945                 950                 955                 960

Gln Gln Asp Leu Asn Asp Pro Ser Lys Tyr Lys Glu Ala Lys Glu Trp
            965                 970                 975

Leu Asp Asn Ala Arg Gln Ala Cys Leu Lys Ser Gly Asn Val His Ile
        980                 985                 990

Ala Asn Leu Cys Lys Val Val Ala Pro Ala Pro Ser Arg Ser Arg Pro
    995                 1000                1005

Glu Pro Val Val Val Cys Leu Arg Gly Lys Ser Gly Gln Gly Lys
    1010                1015                1020

Ser Phe Leu Ala Asn Val Leu Ala Gln Ala Ile Ser Thr His Phe
    1025                1030                1035

Thr Gly Arg Thr Asp Ser Val Trp Tyr Cys Pro Asp Pro Asp
    1040                1045                1050

His Phe Asp Gly Tyr Asn Gln Gln Thr Val Val Met Asp Asp
    1055                1060                1065

Leu Gly Gln Asn Pro Asp Gly Lys Asp Phe Lys Tyr Phe Ala Gln
    1070                1075                1080

Met Val Ser Thr Thr Gly Phe Ile Pro Pro Met Ala Ser Leu Glu
    1085                1090                1095

Asp Lys Gly Lys Pro Phe Asn Ser Lys Val Ile Ile Ala Thr Thr
    1100                1105                1110
```

-continued

Asn Leu Tyr Ser Gly Phe Thr Pro Arg Thr Met Val Cys Pro Asp
    1115                1120                1125

Ala Leu Asn Arg Arg Phe His Phe Asp Ile Asp Val Ser Ala Lys
    1130                1135                1140

Asp Gly Tyr Lys Ile Asn Asn Lys Leu Asp Ile Ile Lys Ala Leu
    1145                1150                1155

Glu Asp Thr His Thr Asn Pro Val Ala Met Phe Gln Tyr Asp Cys
    1160                1165                1170

Ala Leu Leu Asn Gly Met Ala Val Glu Met Lys Arg Met Gln Gln
    1175                1180                1185

Asp Met Phe Lys Pro Gln Pro Leu Gln Asn Val Tyr Gln Leu
    1190                1195                1200

Val Gln Glu Val Ile Glu Arg Val Glu Leu His Glu Lys Val Ser
    1205                1210                1215

Ser His Pro Ile Phe Lys Gln Ile Ser Ile Pro Ser Gln Lys Ser
    1220                1225                1230

Val Leu Tyr Phe Leu Ile Glu Lys Gly Gln His Glu Ala Ala Ile
    1235                1240                1245

Glu Phe Phe Glu Gly Met Val His Asp Ser Ile Lys Glu Glu Leu
    1250                1255                1260

Arg Pro Leu Ile Gln Gln Thr Ser Phe Val Lys Arg Ala Phe Lys
    1265                1270                1275

Arg Leu Lys Glu Asn Phe Glu Ile Val Ala Leu Cys Leu Thr Leu
    1280                1285                1290

Leu Ala Asn Ile Val Ile Met Ile Arg Glu Thr Arg Lys Arg Gln
    1295                1300                1305

Lys Met Val Asp Asp Ala Val Ser Glu Tyr Ile Glu Arg Ala Asn
    1310                1315                1320

Ile Thr Thr Asp Asp Lys Thr Leu Asp Glu Ala Glu Lys Asn Pro
    1325                1330                1335

Leu Glu Thr Ser Gly Ala Ser Thr Val Gly Phe Arg Glu Arg Pro
    1340                1345                1350

Leu Pro Gly Gln Lys Ala Arg Asn Asp Glu Asn Ser Glu Pro Ala
    1355                1360                1365

Gln Pro Ala Glu Glu Gln Pro Gln Ala Glu Gly Pro Tyr Ala Gly
    1370                1375                1380

Pro Met Glu Arg Gln Lys Pro Leu Lys Val Lys Ala Lys Ala Pro
    1385                1390                1395

Val Val Lys Glu Gly Pro Tyr Glu Gly Pro Val Lys Lys Pro Val
    1400                1405                1410

Ala Leu Lys Val Lys Ala Lys Asn Leu Ile Val Thr Glu Ser Gly
    1415                1420                1425

Ala Pro Pro Thr Asp Leu Gln Lys Leu Val Met Gly Asn Thr Lys
    1430                1435                1440

Pro Val Glu Leu Ile Leu Asp Gly Lys Thr Val Ala Ile Cys Cys
    1445                1450                1455

Ala Thr Gly Val Phe Gly Thr Ala Tyr Leu Val Pro Arg His Leu
    1460                1465                1470

Phe Ala Glu Lys Tyr Asp Lys Ile Met Leu Asp Gly Arg Ala Met
    1475                1480                1485

Thr Asp Ser Asp Tyr Arg Val Phe Glu Phe Glu Ile Lys Val Lys
    1490                1495                1500

Gly Gln Asp Met Leu Ser Asp Ala Ala Leu Met Val Leu His Arg

-continued

```
            1505                1510                1515
Gly Asn Arg Val Arg Asp Ile Thr Lys His Phe Arg Asp Thr Ala
            1520                1525                1530
Arg Met Lys Lys Gly Thr Pro Val Val Gly Val Ile Asn Asn Ala
            1535                1540                1545
Asp Val Gly Arg Leu Ile Phe Ser Gly Glu Ala Leu Thr Tyr Lys
            1550                1555                1560
Asp Ile Val Val Cys Met Asp Gly Asp Thr Met Pro Gly Leu Phe
            1565                1570                1575
Ala Tyr Lys Ala Ala Thr Lys Ala Gly Tyr Cys Gly Gly Ala Val
            1580                1585                1590
Leu Ala Lys Asp Gly Ala Asp Thr Phe Ile Val Gly Thr His Ser
            1595                1600                1605
Ala Gly Gly Asn Gly Val Gly Tyr Cys Ser Cys Val Ser Arg Ser
            1610                1615                1620
Met Leu Leu Lys Met Lys Ala His Val Asp Pro Glu Pro His His
            1625                1630                1635
Glu Gly Leu Ile Val Asp Thr Arg Asp Val Glu Glu Arg Val His
            1640                1645                1650
Val Met Arg Lys Thr Lys Leu Ala Pro Thr Val Ala Tyr Gly Val
            1655                1660                1665
Phe Arg Pro Glu Phe Gly Pro Ala Ala Leu Ser Asn Lys Asp Pro
            1670                1675                1680
Arg Leu Asn Asp Gly Val Val Leu Asp Glu Val Ile Phe Ser Lys
            1685                1690                1695
His Lys Gly Asp Thr Lys Met Ser Glu Glu Asp Lys Ala Leu Phe
            1700                1705                1710
Arg Arg Cys Ala Ala Asp Tyr Ala Ser Arg Leu His Ser Val Leu
            1715                1720                1725
Gly Thr Ala Asn Ala Pro Leu Ser Ile Tyr Glu Ala Ile Lys Gly
            1730                1735                1740
Val Asp Gly Leu Asp Ala Met Glu Pro Asp Thr Ala Pro Gly Leu
            1745                1750                1755
Pro Trp Ala Leu Gln Gly Lys Arg Arg Gly Ala Leu Ile Asp Phe
            1760                1765                1770
Glu Asn Gly Thr Val Gly Pro Glu Val Glu Ala Ala Leu Lys Leu
            1775                1780                1785
Met Glu Lys Arg Glu Tyr Lys Phe Ala Cys Gln Thr Phe Leu Lys
            1790                1795                1800
Asp Glu Ile Arg Pro Met Glu Lys Val Arg Ala Gly Lys Thr Arg
            1805                1810                1815
Ile Val Asp Val Leu Pro Val Glu His Ile Leu Tyr Thr Arg Met
            1820                1825                1830
Met Ile Gly Arg Phe Cys Ala Gln Met His Ser Asn Asn Gly Pro
            1835                1840                1845
Gln Ile Gly Ser Ala Val Gly Cys Asn Pro Asp Val Asp Trp Gln
            1850                1855                1860
Arg Phe Gly Thr His Phe Ala Gln Tyr Arg Asn Val Trp Asp Val
            1865                1870                1875
Asp Tyr Ser Ala Phe Asp Ala Asn His Cys Ser Asp Ala Met Asn
            1880                1885                1890
Ile Met Phe Glu Glu Val Phe Arg Thr Glu Phe Gly Phe His Pro
            1895                1900                1905
```

Asn Ala Glu Trp Ile Leu Lys Thr Leu Val Asn Thr Glu His Ala
1910                1915                1920

Tyr Glu Asn Lys Arg Ile Thr Val Glu Gly Gly Met Pro Ser Gly
1925                1930                1935

Cys Ser Ala Thr Ser Ile Ile Asn Thr Ile Leu Asn Asn Ile Tyr
1940                1945                1950

Val Leu Tyr Ala Leu Arg Arg His Tyr Glu Gly Val Glu Leu Asp
1955                1960                1965

Thr Tyr Thr Met Ile Ser Tyr Gly Asp Asp Ile Val Val Ala Ser
1970                1975                1980

Asp Tyr Asp Leu Asp Phe Glu Ala Leu Lys Pro His Phe Lys Ser
1985                1990                1995

Leu Gly Gln Thr Ile Thr Pro Ala Asp Lys Ser Asp Lys Gly Phe
2000                2005                2010

Val Leu Gly His Ser Ile Thr Asp Val Thr Phe Leu Lys Arg His
2015                2020                2025

Phe His Met Asp Tyr Gly Thr Gly Phe Tyr Lys Pro Val Met Ala
2030                2035                2040

Ser Lys Thr Leu Glu Ala Ile Leu Ser Phe Ala Arg Arg Gly Thr
2045                2050                2055

Ile Gln Glu Lys Leu Ile Ser Val Ala Gly Leu Ala Val His Ser
2060                2065                2070

Gly Pro Asp Glu Tyr Arg Arg Leu Phe Glu Pro Phe Gln Gly Leu
2075                2080                2085

Phe Glu Ile Pro Ser Tyr Arg Ser Leu Tyr Leu Arg Trp Val Asn
2090                2095                2100

Ala Val Cys Gly Asp Ala
    2105

<210> SEQ ID NO 19
<211> LENGTH: 40
<212> TYPE: PRT
<213> ORGANISM: Artificial Sequence
<220> FEATURE:
<223> OTHER INFORMATION: Foot-and-mouth disease virus

<400> SEQUENCE: 19

Gly Leu Ile Val Asp Thr Arg Asp Val Glu Glu Arg Val His Val Met
1               5                   10                  15

Arg Lys Thr Lys Leu Ala Pro Thr Val Ala His Gly Val Phe Asn Pro
            20                  25                  30

Glu Phe Gly Pro Ala Ala Leu Ser
        35                  40

<210> SEQ ID NO 20
<211> LENGTH: 40
<212> TYPE: PRT
<213> ORGANISM: Artificial Sequence
<220> FEATURE:
<223> OTHER INFORMATION: Foot-and-mouth disease virus

<400> SEQUENCE: 20

Gly Leu Ile Val Asp Thr Arg Asp Val Glu Glu Arg Val His Val Met
1               5                   10                  15

Arg Lys Thr Lys Leu Ala Pro Thr Val Ala Tyr Gly Val Phe Arg Pro
            20                  25                  30

Glu Phe Gly Pro Ala Ala Leu Ser

```
<210> SEQ ID NO 21
<211> LENGTH: 24
<212> TYPE: PRT
<213> ORGANISM: Artificial Sequence
<220> FEATURE:
<223> OTHER INFORMATION: Foot-and-mouth disease virus

<400> SEQUENCE: 21

Gly Pro Tyr Ala Gly Pro Met Glu Arg Gln Lys Pro Leu Lys Val Arg
1               5                   10                  15

Ala Lys Ala Pro Val Val Lys Glu
            20

<210> SEQ ID NO 22
<211> LENGTH: 24
<212> TYPE: PRT
<213> ORGANISM: Artificial Sequence
<220> FEATURE:
<223> OTHER INFORMATION: Foot-and-mouth disease virus

<400> SEQUENCE: 22

Gly Pro Tyr Ala Gly Pro Met Glu Pro Val Lys Val Leu Lys Val Arg
1               5                   10                  15

Ala Lys Ala Pro Val Val Lys Glu
            20

<210> SEQ ID NO 23
<211> LENGTH: 7589
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 23
ttgaaagggg gcgctagggt ctcaccccta gcatgccaac gacagtcccc gcgttgcact      60
ccacactcac gttgtgcgtg cgcggagctc gatggactat cgttcaccca cctacagctg    120
gactcacggc accgtgtggc cacttggctg gattgtgcgg acgaacaccg cttgcgcttc    180
tcgcgtgacc ggttagtact ctcaccacct tccgcccact tggttgttag cgctgtcttg    240
ggcactcctg ttgggggccg ttcgacgctc cgcgagtttc cccgcacggc aactacggtg    300
atggggccgt accgcgcggg ctgatcgcct ggtgtgcttc ggctgtcacc cgaagcctac    360 cttttcacccc ccccccccc ccccccccc ccccccccc cccccccctaa gttctaccgt    420 cgttcccgac gtaaagggat gtaaccacaa gcttactacc gcctttcccg gcgttaaagg    480
gatgtaacca caagacttac cttcacccgg aagtaaaacg gcaacttcac acagttttgc    540
ccgttttcat gagaaatggg acgtctgcgc acgaaacgcg ccgtcgcttg aggaggactt    600
gtacaaacac gatctaagca ggtttcccca actgacacaa ccgtgcaatt tgaaactcc    660 gcctgggctt tccaggtcta gagggtgac gctttgtact gtgtttgact ccacgttcga    720
tccactggcg agtgttagta acaacactgc tgcttcgtag cggagcatga cggccgtggg    780
accccccccc ttggtaacaa ggacccacgg ggccaaaagc cacgtccgaa tggacccgtc    840
atgtgtgcaa acccagcaca gtagctttgt tgtgaaactc actttaaagt gacattgata    900
ctggtactca agcactggtg acaggctaag gatgccttc aggtacccg aggtaacacg    960 tgacactcgg gatctgagaa ggggaccggg gcttctataa aagcgccgg tttaaaaagc   1020
```

-continued

```
ttctatgtct gaataggtga ccggaggccg gcacctttct tttaattaca ctggacttat    1080
gaacacaact gattgtttta tcgctttggt acacgctatc agagagatca gagcattttt    1140
cctaccacga gccacaggaa tgggggccgg ccaatccagt ccggcaaccg ggtcacagaa    1200
ccaatctggc aacactggaa gcatcattaa caactactac atgcaacagt accagaattc    1260
catggacaca cagcttggtg acaacgctat tagcggaggt tccaacgaag gttccacgga    1320
taccacttcc acacacacaa acaacaccca aacaacgac  tggttctcgc gcctggcaag    1380
ttctgcattc agtggtctct tggtgcact  tttggctgac aagaagacag aagagacaac    1440
tctgcttgaa gaccgcattc tcaccaccag gaacggccac acaacatcga cgacacagtc    1500
gagcgttggc gtaacatacg gttacgctgt ggccgaggac gcggtgtctg acccaatac     1560 ctcgggtcta gagactcgtg ttcaacaggc agaacggttt ttcaagaaac acctgtttga    1620
ctggacaccg aacttggcat ttggacactg ttactacctg gaacttccca ctgaacacaa    1680
aggcgtgtac ggcagtctca tgggctcgta cgcctacatg agaaatggat gggacataga    1740
ggtgactgct gttggaaacc aattcaacgg tggttgtctc cttgtcgcgc tcgtgccaga    1800
gctgaaggaa ctcgacacgc gacagaagta ccagctgacc ctctttcccc accagttcat    1860
caacccacga ccaacatga  cggcccacat caacgtgccg tacgtgggta tcaacaggta    1920
cgaccagtac gccctccaca agccgtggac gcttgttgtg atggtggtag ccccactcac    1980
cgtcaaaact ggtggttctg aacagatcaa ggtttacatg aatgcagcgc aacctacgt     2040 gcatgtggcg ggagagctgc cctcgaaaga gggaatagtt cccgtcgcgt gtgcggacgg    2100
ttacggcaac atggtgacca cggacccgaa gacggccgat ccagtttacg ggaaagtgtt    2160 caacccccc  aggacaaacc tccctgggcg cttcacgaac ttccttgatg ttgcggaggc    2220
atgtccaact ttcctccgct ttggagaagt accatttgtg aagacggtga actctggtga    2280
ccgcttgctg gccaagttcg acgtgtccct cgctgcaggg cacatgtcca cacctactt     2340 ggctggcctg gcgcagtact acacacagta cagcggcacc atgaacgtcc acttcatgtt    2400
caccgggccc acggatgcta agcccgata  catggtggct tatgtccccc ctggcatgac    2460
accgcccacg gaccctgagc acgccgcaca ctgcattcac tctgagtggg atactggtct    2520
taactctaag tttaccttt  ccataccta  cctctctgct gctgactatg cctacactgc    2580
ttctgacgtg gcggagacca cgagtgtgca gggatgggtg tgtatctatc agatcaccca    2640
cggcaaggct gagggagacg cactggtcgt ttctgtcagc gccggcaaag actttgagtt    2700
tcgcttgcct gttgacgcac gccagcaaac caccaccact ggcgaatcag cagatccagt    2760
cacaaccacg gttgagaact atggaggaga gactcagaca gccagacggc ttcacactga    2820
cgtcgccttc attcttgaca ggtttgtgaa actcactgct cccaagaaca tccaaaccct    2880
cgatctcatg cagatcccct cacacacgct ggttggagca ctacttcgtt ctgcgacgta    2940
ctacttctca gacctggagg tcgcgcttgt ccacacaggc ccggtcacct gggtgcccaa    3000
cggcgcgccc aaggatgctc taaacaacca gaccaaccca actgcctatc agaagcaacc    3060
catcacccgc ctggcactcc cctacaccgc ccccatcgt  gtgctggcaa cagtgtacaa    3120
cgggaagacg gcgtacgggg aaacgacctc aaggcgcggc gacatggcgg ccctcgcaca    3180
aaggttgagc gctcggctgc ccacctcctt caactacggc gccgtgaagg ccgacaccat    3240
cactgagctt ttgatccgca tgaagcgcgc ggagacatat tgccctaggc ctttactagc    3300
ccttgacacc actcaggacc gccgcaaaca ggagatcatt gcacctgaga agcagcttct    3360
gaattttgac ctgcttaagc tagccggaga cgttgagtcc aaccctgggc ccttcttctt    3420
```

```
ctccgacgtt aggtcaaact tttccaagct ggtagacaca atcaaccaga tgcaggaaga    3480
catgtccaca aagcacggac ctgactttaa ccgttggtg tccgcttttg aggagttggc    3540
cactggagtg aaagccatca ggaccggtct tgacgaggcc aagccctggt acaagcttat    3600
caagctcctg agccgcctgt cgtgcatggc cgctgtggca gcacggtcaa aggacccagt    3660
ccttgtggcc atcatgctgg ctgacaccgg tctcgagatt ctggacagca ccttcgtcgt    3720
gaagaagatc tccgactcgc tctccagtct cttccacgtg ccggcccccg tcttcagttt    3780
cggagccccg attctgttag ccgggttggt caaggtcgcc tcgagtttct tccggtccac    3840
gcccgaagac cttgagagag cagagaaaca gctcaaagca cgtgacatca acgacatttt    3900
cgccattctc aagaacggcg agtggctggt caaattgatc cttgccatcc gcgactggat    3960
caaggcatgg atagcctcag aagaaaagtt tgtcaccacg acagacttgg tacctagcat    4020
ccttgaaaaa cagcaggacc tcaacgaccc aagcaagtac aaggaagcca aggagtggct    4080
cgacaacgcg cgccaagcgt gtttgaagag cgggaacgtc cacattgcca acctgtgcaa    4140
agtggtcgcc ccggcaccca gcaggtcgag acccgagccc gtggtcgttt gcctccgtgg    4200
caagtccggt cagggcaaga gtttccttgc aaacgtgctc gcacaagcaa tctctaccca    4260
tttcactggc aggaccgatt cagtttggta ctgcccgcct gaccctgacc acttcgacgg    4320
ttacaaccaa cagactgtcg ttgtgatgga cgatttgggc cagaaccccg acggcaaaga    4380
cttcaagtac ttcgcccaaa tggtttcaac acggggttc atcccgccca tggcatcgct    4440
tgaggataaa ggcaaaccct tcaacagtaa ggtcatcata gcaaccacca acctgtactc    4500
gggcttcacc ccgaggacta tggtgtgccc tgatgccctg aaccggaggt ttcactttga    4560
catcgacgtg agcgccaagg acgggtacaa aattaacaac aaattggaca tcatcaaagc    4620
acttgaagat actcacacca acccagtggc aatgtttcag tacgactgtg cccttctcaa    4680
cggcatggct gttgaaatga agagaatgca acaagatatg ttcaagcctc aaccacccct    4740
tcagaacgtg taccaactgg ttcaagaggt gattgagcgg gtggagctcc acgagaaggt    4800
gtcgagccac ccgattttca aacagatctc aattccttcc caaaaatccg tgttgtactt    4860
cctcattgag aaaggacagc acgaggcagc aattgaattc tttgagggca tggtgcacga    4920
ctccatcaag gaggagctcc ggccgctcat ccaacaaacc tcatttgtga acgcgctttt    4980
taagcgcctg aaggaaaact ttgagattgt tgccctatgt ctgaccctcc tggccaacat    5040
agtgatcatg atccgcgaaa ctcgcaagag acagaagatg gtggacgatg cagtgagtga    5100
gtacattgag agagcaaaca tcaccaccga cgacaagact cttgatgagg cggaaaagaa    5160
ccctctggaa accagcggtg ccagcaccgt cggcttcaga gagagacctc tcccaggcca    5220
aaaggcgcgt aatgacgaga actccgagcc cgcccagcct gctgaagagc aaccacaagc    5280
tgaaggaccc tacgctggcc cgatggagag accagttaaa gttaaagtga agcaaaagc    5340 cccggtcgtt aaggaaggac cttacgaggg accggtgaag aagcctgttg ctttgaaagt    5400
gaaagctaag aacttgatcg tcactgagag tggtgccccca ccgaccgact gcaaaagtt    5460 ggtcatgggc aacaccaagc ccgttgagct catccttgac gggaagacgg tagccatttg    5520
ctgtgctact ggagttttcg gcactgctta cctcgtgcct cgtcatcttt tcgcagaaaa    5580
gtacgacaag atcatgttgg acggcagagc catgacagat agtgactaca gagtgtttga    5640
gtttgagatt aaagtaaaag gacaggacat gctctcagac gctgcgctca tggtgctcca    5700
ccgtgggaat cgcgtgagag acatcacgaa acactttcgt gacacagcaa gaatgaagaa    5760
```

```
aggcaccccc gtcgttggtg tgatcaacaa cgccgatgtc gggagactga tttctctgg      5820
tgaagccctt acctacaagg acattgtagt gtgcatggat ggagacacca tgcctgggct      5880
ctttgcctac aaagccgcaa ccaaggctgg ttattgcgga ggagccgtcc tcgctaagga      5940
cggggctgac acgttcatcg ttggcaccca ctccgctgga ggcaatggcg ttggatactg      6000
ctcttgcgtt tccaggtcca tgcttctcaa gatgaaggca cacgttgacc ccgaaccaca      6060
ccacgagggg ttgattgttg acaccagaga tgtggaagag cgcgttcacg tgatgcgcaa      6120
aaccaagctt gcacccaccg ttgcgtacgg tgtgttccgt cctgagttcg gcctgccgc      6180
cttgtccaac aaggacccgc gcctgaacga cggtgttgtc ctcgacgaag tcatcttctc      6240
caaacacaag ggagacacaa agatgtctga ggaagacaaa gcgctgttcc gccgctgtgc      6300
tgctgactac gcgtcacgcc tgcacagcgt gttgggtacg gcaaatgccc cactgagcat      6360
ctacgaggca attaaaggcg ttgatggact cgacgcaatg gaaccagaca ccgcacccgg      6420
cctcccctgg gcactccagg ggaagcgccg tggcgcgctc atcgacttcg agaacggcac      6480
tgttggaccc gaagttgagg ctgccttgaa gctcatggaa aaagagaat acaagtttgc      6540
ttgccaaacc ttcctgaagg acgagattcg cccgatggag aaagtacgtg ccggtaagac      6600
tcgcattgtc gacgtcctac ctgttgaaca catcctctac accaggatga tgattggcag      6660
attttgtgca caaatgcact caaacaacgg accccaaatt ggctcggcgg tcggttgtaa      6720
ccctgatgtt gattggcaaa gatttggcac acacttcgcc caatacgaa acgtgtggga      6780
tgtggactat tcggccttcg atgctaacca ctgcagtgac gccatgaaca tcatgtttga      6840
ggaagtgttt cgcacagaat tcgggttcca cccaaacgct gagtggatcc tgaagactct      6900
cgtgaacacg gaacacgcct atgagaacaa acgcatcact gttgaaggcg ggatgccatc      6960
tggttgttcc gcaacaagca tcatcaacac aatttttgaac aacatctacg tgctctacgc      7020
tttgcgtaga cactatgagg gagttgagct ggacacttac accatgatct cttacggaga      7080
cgatatcgtg gtggcaagtg attacgattt ggactttgag gctctcaagc ccacttcaa      7140
atcccttggt caaaccatca ctccagctga caaaagcgac aaaggttttg ttcttggtca      7200
ctccattact gatgtcactt tcctcaaaag acacttccac atggattatg aactggggtt      7260
ttacaaacct gtgatggcct caaagaccct tgaggctatc ctctcctttg cacgccgtgg      7320
gaccatacag gagaagttga tctccgtggc aggactcgct gttcactctg accagacga      7380
gtaccggcgt ctcttcgagc cctttcaagg cctcttcgag attccaagct acagatcact      7440
ttacctgcgt tgggtgaacg ccgtgtgcgg cgacgcataa tccctcagag actacattgg      7500
catactgttt ctgaggcgcg cgacgccgta ggagtgaaaa gcctgaaagg cttttcccg      7560
cttcctattc caaaaaaaaa aaaaaaaaa                                       7589
```

<210> SEQ ID NO 24
<211> LENGTH: 7600
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 24

```
ttgaaagggg gcgctagggt ctcaccccta gcatgccaac gacagtcccc gcgttgcact       60
ccacactcac gttgtgcgtg cgcggagctc gatggactat cgttcaccca cctacagctg      120
gactcacggc accgtgtggc cacttggctg gattgtgcgg acgaacaccg cttgcgcttc      180
```

```
tcgcgtgacc ggttagtact ctcaccacct tccgcccact tggttgttag cgctgtcttg    240
ggcactcctg ttgggggccg ttcgacgctc cgcgagtttc cccgcacggc aactacggtg    300
atggggccgt accgcgcggg ctgatcgcct ggtgtgcttc ggctgtcacc cgaagcctac    360
cttttcacccc cccccccccc cccccccccc ccccccctaa gttctaccgt               420
cgttcccgac gtaaagggat gtaaccacaa gcttactacc gcctttcccg gcgttaaagg    480
gatgtaacca caagacttac cttcacccgg aagtaaaacg gcaacttcac acagttttgc    540
ccgttttcat gagaaatggg acgtctgcgc acgaaacgcg ccgtcgcttg aggaggactt    600
gtacaaacac gatctaagca ggtttcccca actgacacaa accgtgcaat ttgaaactcc    660
gcctgggctt tccaggtcta gagggtgacg ctttgtact gtgtttgact ccacgttcga     720
tccactggcg agtgttagta acaacactgc tgcttcgtag cggagcatga cggccgtggg    780
accccccccc ttggtaacaa ggaccacgg ggccaaaagc cacgtccgaa tggacccgtc     840
atgtgtgcaa acccagcaca gtagctttgt tgtgaaactc actttaaagt gacattgata    900
ctggtactca agcactggtg acaggctaag gatgcccttc aggtacccg aggtaacacg     960
tgacactcgg gatctgagaa ggggaccggg gcttctataa aagcgcccgg tttaaaaagc   1020
ttctatgtct gaataggtga ccggaggccg gcaccttct tttaattaca ctggacttat    1080
gaacacaact gattgtttta tcgctttggt acacgctatc agagagatca gagcattttt   1140
cctaccacga gccacaggaa tgggggccgg ccaatccagt ccggcaaccg ggtcacaaaa   1200
ccaatcaggc aacactggta gtatcatcaa caactactac atgcagcagt accagaactc   1260
catggataca caacttggcg acaacgccat tagcggtggt tccaacgagg gctccactga   1320
cactacctcc acacacacaa ccaacacaca gaacaatgac tggttttcaa agctggccag   1380
ttctgccttc agcggtctct tcggcgctct tctcgctgac aaaaagacag aggagactac   1440
cctcctggag gaccgcatcc ttaccacccg caacggacac accacctcga caacccagtc   1500
gagtgtgggt gtcacctacg ggtactccac tggtgaagac cacgtctctg gacctaacac   1560
atctggcctg gagacgcgag tggtacaggc agagagattc ttcaagaaac acttgtttga   1620
ttggacaact gataaagctt ttggacacct ggaaaaactg gaactccca ccgaacacaa    1680
gggtgtctac gggcacttgg tggactcttt cgcatacatg agaaatggct gggacgtgga   1740
ggtgaccgcc gttggcaacc agttcaacgg tgggtgtctc ctggtggcca tggtacctga   1800
gtggaaagag tttaccctc gtgagaaata ccagctcacc ctgtttccac accaatttat    1860
caacccaga accaacatga cagcccacat cacggtcccg taccttggtg tcaataggta    1920
tgaccagtac aaacagcaca aaccctggac actggtcgtg atggtggttt cgccactgac   1980
caccagcagc attggggcct cacagattaa ggtctacgcc aacattgccc caaccttcgt   2040
tcacgtggcc ggcgagctcc catcgaaaga agggatcgtg ccggttgctt gtacagacgg   2100
gtacggtggc ctggtgacaa cagacccgaa aacagctgac cctgtttatg gtatggtgta   2160
caacccgccc agaaccaact accctgggcg ctttacaaac ttgttggacg tggccgaggc   2220
ttgcccgacc ttcctctgtt ttgacgacgg gaaaccgtac gttgtgacaa ggacggacga   2280
ccaacgcctc ctggccaagt ttgacgtttc ccttgctgca aagcacatgt caaacaccta   2340
cctctcaggg atagcacagt actacacgca gtactctggc actatcaatc tgcatttcat   2400
gttcactggc tctactgaat caaaggcccg gtacatggtg gcgtacattc cacctggcat   2460
ggacaaccca ccgacacac ctgagaaggc tgcacattgc atccacgccg agtgggacac    2520
cgggctgaac tccaaattta cttttttctat cccgtacgtg tctgctgcag actacgcata   2580
```

```
cactgcgtct gacgtggcag aaacaacaaa cgtacagggg tgggtctgca tataccaaat   2640
cactcacggg aaggctgaac aggacactct ggtcgtgtcg gtcagcgccg gcaaggactt   2700
tgaactgcgc ctcccaattg accccgcac gcaaaccacc actgccgggg agtcagcaga    2760
ccctgtcacc accaccgttg agaactacgg tggtgagaca caggctcagc gacgtcagca   2820
cactgacgtc ggcttcatca tggacaggtt tgcgaaaatc agccccgtga gccccacgca   2880
cgtcattgac ctcatgcaaa cacaccaaca cgcgttggtg ggtgcccttt tgcgtgcagc   2940
cacgtactac ttctccgatc tggagattgt ggtgcgtcat gatggcaact tgacgtgggt   3000
gcccaatgga gcacctgtag aagccttggc caacacaagc aaccccaccg cctaccacaa   3060
gcagccattt acgagacttg cgctccctta caccgcgccg caccgagtgt tggcaacagt   3120
gtataacgga gtaagcaagt actctacaac tggtaatggc agaaggggtg acctggggcc   3180
tcttgcggcg cgggtcgccg cacagctccc cagctctttc aattttggtg caattcgggc   3240
cacgaccgtc cacgagcttc tcgtgcgcat gaaacgtgcc gagctctact gtcccaggcc   3300
tctgctggca gtggaagtgt tgtcgcagga cagacacaag caaagatca ttgcacctgc    3360 aaagcaactt ctgaattttg acctgcttaa gctagccgga gacgttgagt ccaaccctgg   3420
gcccttcttc ttctccgacg ttaggtcaaa cttttccaag ctggtagaca caatcaacca   3480
gatgcaggaa gacatgtcca caaagcacgg acctgacttt aaccggttgg tgtccgcttt   3540
tgaggagttg gccactggag tgaaagccat caggaccggt cttgacgagg ccaagccctg   3600
gtacaagctt atcaagctcc tgagccgcct gtcgtgcatg gccgctgtgg cagcacggtc   3660
aaaggaccca gtccttgtgg ccatcatgct ggctgacacc ggtctcgaga ttctggacag   3720
caccttcgtc gtgaagaaga tctccgactc gctctccagt ctcttccacg tgccggcccc   3780
cgtcttcagt ttcggagccc cgattctgtt agccgggttg gtcaaggtcg cctcgagttt   3840
cttccggtcc acgcccgaag accttgagag agcagagaaa cagctcaaag cacgtgacat   3900
caacgacatt ttcgccattc tcaagaacgg cgagtggctg gtcaaattga tccttgccat   3960
ccgcgactgg atcaaggcat ggatagcctc agaagaaaag tttgtcacca cgacagactt   4020
ggtacctagc atccttgaaa aacagcagga cctcaacgac ccaagcaagt acaaggaagc   4080
caaggagtgg ctcgacaacg cgcgccaagc gtgtttgaag agcgggaacg tccacattgc   4140
caacctgtgc aaagtggtcg ccccggcacc cagcaggtcg agacccgagc ccgtggtcgt   4200
ttgcctccgt ggcaagtccg gtcagggcaa gagtttcctt gcaaacgtgc tcgcacaagc   4260
aatctctacc catttcactg gcaggaccga ttcagtttgg tactgcccgc ctgaccctga   4320
ccacttcgac ggttacaacc aacagactgt cgttgtgatg gacgatttgg ccagaaccc    4380 cgacggcaaa gacttcaagt acttcgccca aatggtttca acaacggggt tcatcccgcc   4440
catggcatcg cttgaggata aaggcaaacc cttcaacagt aaggtcatca tagcaaccac   4500
caacctgtac tcgggcttca ccccgaggac tatggtgtgc cctgatgccc tgaaccggag   4560
gtttcacttt gacatcgacg tgagcgccaa ggacgggtac aaaattaaca acaaattgga   4620
catcatcaaa gcacttgaag atactcacac caacccagtg gcaatgtttc agtacgactg   4680
tgcccttctc aacggcatgg ctgttgaaat gaagagaatg caacaagata tgttcaagcc   4740
tcaaccaccc cttcagaacg tgtaccaact ggttcaagag gtgattgagc gggtggagct   4800
ccacgagaag gtgtcgagcc acccgatttt caaacagatc tcaattcctt cccaaaaatc   4860
cgtgttgtac ttcctcattg agaaaggaca gcacgaggca gcaattgaat ctttgagggg   4920
```

```
catggtgcac gactccatca aggaggagct ccggccgctc atccaacaaa cctcatttgt    4980
gaaacgcgct tttaagcgcc tgaaggaaaa ctttgagatt gttgcccctat gtctgaccct    5040 cctggccaac atagtgatca tgatccgcga aactcgcaag agacagcaga tggtggacga    5100
tgcagtgagt gagtacattg agagagcaaa catcaccacc gacgacaaga ctcttgatga    5160
ggcggaaaag aaccctctgg aaaccagcgg tgccagcacc gtcggcttca gagagagacc    5220
tctcccaggc caaaggcgc gtaatgacga gaactccgag cccgcccagc ctgctgaaga    5280
gcaaccacaa gctgaaggac cctacgctgg cccgatggag agaccagtta aagttaaagt    5340
gaaagcaaaa gccccggtcg ttaaggaagg accttacgag ggaccggtga agaagcctgt    5400
tgctttgaaa gtgaaagcta agaacttgat cgtcactgag agtggtgccc caccgaccga    5460
cttgcaaaag ttggtcatgg gcaacaccaa gcccgttgag ctcatccttg acgggaagac    5520
ggtagccatt tgctgtgcta ctggagtttt cggcactgct tacctcgtgc ctcgtcatct    5580
tttcgcagaa aagtacgaca agatcatgtt ggacggcaga gccatgacag atagtgacta    5640
cagagtgttt gagtttgaga ttaaagtaaa aggacaggac atgctctcag acgctgcgct    5700
catggtgctc accgtgggga atcgcgtgag agacatcacg aaacactttc gtgacacagc    5760
aagaatgaag aaaggcaccc ccgtcgttgg tgtgatcaac aacgccgatg tcgggagact    5820 gatttttctct ggtgaagccc ttacctacaa ggacattgta gtgtgcatgg atggagacac    5880
catgcctggg ctctttgcct acaaagccgc aaccaaggct ggttattgcg gaggagccgt    5940
cctcgctaag gacggggctg acacgttcat cgttggcacc cactccgctg gaggcaatgg    6000
cgttggatac tgctccttgcg tttccaggtc catgcttctc aagatgaagg cacacgttga    6060
ccccgaacca caccacgagg ggttgattgt tgacaccaga gatgtggaag agcgcgttca    6120 cgtgatcgc aaaaccaagc ttgcacccac cgttgcgtac ggtgtgttcc gtcctgagtt    6180
cgggcctgcc gccttgtcca acaaggaccc gcgcctgaac gacggtgttg tcctcgacga    6240
agtcatcttc tccaaacaca agggagacac aaagatgtct gaggaagaca aagcgctgtt    6300
ccgccgctgt gctgctgact acgcgtcacg cctgcacagc gtgttgggta cggcaaatgc    6360
cccactgagc atctacgagg caattaaagg cgttgatgga ctcgacgcaa tggaaccaga    6420
caccgcaccc ggcctcccct gggcactcca ggggaagcgc cgtggcgcgc tcatcgactt    6480
cgagaacggc actgttggac ccgaagttga ggctgccttg aagctcatgg agaaaagaga    6540
atacaagttt gcttgccaaa ccttcctgaa ggacgagatt cgcccgatgg agaaagtacg    6600
tgccggtaag actcgcattg tcgacgtcct acctgttgaa cacatcctct acaccaggat    6660
gatgattggc agattttgtg cacaaatgca ctcaaacaac ggaccccaaa ttggctcggc    6720
ggtcggttgt aaccctgatg ttgattggca aagatttggc acacacttcg cccaatacag    6780
aaacgtgtgg gatgtggact attcggcctt cgatgctaac cactgcagtg acgccatgaa    6840
catcatgttt gaggaagtgt ttcgcacaga attcggttc cacccaaacg ctgagtggat    6900
cctgaagact ctcgtgaaca cggaacacgc ctatgagaac aaaacgcatca ctgttgaagg    6960 cgggatgcca tctggttgtt ccgcaacaag catcatcaac acaattttga acaacatcta    7020
cgtgctctac gctttgcgta gacactatga gggagttgag ctggacactt acaccatgat    7080
ctcttacgga gacgatatcg tggtggcaag tgattacgat ttggactttg aggctctcaa    7140
gccccacttc aaatcccttg gtcaaaccat cactccagct gacaaaagcg acaaaggttt    7200
tgttcttggt cactccatta ctgatgtcac tttcctcaaa agacacttcc acatggatta    7260
tggaactggg ttttacaaac ctgtgatggc ctcaaagacc cttgaggcta tcctctcctt    7320
```

| | |
|---|---|
| tgcacgccgt gggaccatac aggagaagtt gatctccgtg gcaggactcg ctgttcactc | 7380 |
| tggaccagac gagtaccggc gtctcttcga gcccttttcaa ggcctcttcg agattccaag | 7440 |
| ctacagatca ctttacctgc gttgggtgaa cgccgtgtgc ggcgacgcat aatccctcag | 7500 |
| agactacatt ggcatactgt ttctgaggcg cgcgacgccg taggagtgaa aagcctgaaa | 7560 |
| gggcttttcc cgcttcctat tccaaaaaaa aaaaaaaaa | 7600 |

<210> SEQ ID NO 25
<211> LENGTH: 7597
<212> TYPE: DNA
<213> ORGANISM: Artificial Sequence
<220> FEATURE:
<223> OTHER INFORMATION: Fusion Nucleotide Sequence containing O1 Campos strain of FMD (complete genome)

<400> SEQUENCE: 25

| | |
|---|---|
| ttgaaagggg gcgctagggt ctcacccta gcatgccaac gacagtcccc gcgttgcact | 60 |
| ccacactcac gttgtgcgtg cgcggagctc gatggactat cgttcaccca cctacagctg | 120 |
| gactcacggc accgtgtggc cacttggctg gattgtgcgg acgaacaccg cttgcgcttc | 180 |
| tcgcgtgacc ggttagtact ctcaccacct tccgcccact tggttgttag cgctgtcttg | 240 |
| ggcactcctg ttgggggccg ttcgacgctc cgcgagtttc cccgcacggc aactacggtg | 300 |
| atggggccgt accgcgcggg ctgatcgcct ggtgtgcttc ggctgtcacc cgaagcctac | 360 |
| cttttcacccc ccccccccc ccccccccc ccccccctaa gttctaccgt | 420 |
| cgttcccgac gtaagggat gtaaccacaa gcttactacc gcctttcccg gcgttaaagg | 480 |
| gatgtaacca caagacttac cttcacccgg aagtaaaacg gcaacttcac acagttttgc | 540 |
| ccgttttcat gagaaatggg acgtctgcgc acgaaacgcg ccgtcgcttg aggaggactt | 600 |
| gtacaaacac gatctaagca ggtttcccca actgacacaa accgtgcaat ttgaaactcc | 660 |
| gcctgggctt tccaggtcta gagggggtgac actttgtact gtgtttgact ccacgttcga | 720 |
| tccactggcg agtgttagta acaacactgc tgcttcgtag cggagcatga cggccgtggg | 780 |
| acccccccc ttggtaacaa ggacccacgg ggccaaaagc cacgtccgaa tggacccgtc | 840 |
| atgtgtgcaa acccagcaca gtagctttgt tgtgaaactc actttaaagt gacattgata | 900 |
| ctggtactca agcactggtg acaggctaag gatgccctc aggtaccccg aggtaacacg | 960 |
| tgacactcgg gatctgagaa ggggaccggg gcttctataa aagcgcccgg tttaaaaagc | 1020 |
| ttctatgtct gaataggtga ccggaggccg gcacctttct tttaattaca ctggacttat | 1080 |
| gaacacaact gattgtttta tcgctttggt acacgctatc agagagatca gagcattttt | 1140 |
| cctaccacga gccacaggaa tgggggccgg ccaatccagt ccggcgaccg gctcgcagaa | 1200 |
| ccaatctggc aacactggca gcataattaa caactactac atgcagcaat accagaactc | 1260 |
| catggacaca cagcttggtg acaacgcaat cagtggaggc tctaacgagg gctccaccga | 1320 |
| cacaacctcc acccacacaa ccaacaccca gaacaatgac tggttctcca aacttgcaag | 1380 |
| ctctgctttc agcggtcttt tcggcgctct tctcgccgac aagaagacag aggagaccac | 1440 |
| tctcctcgaa gaccgcatcc tcaccacccg taacggccac accacgtcga caacccagtc | 1500 |
| aagcgttgga gtcacatacg ggtacgcaac agctgaggat tttgtgagcg gaccgaacac | 1560 |
| ttccggtctc gagaccagag ttgtgcaggc agaacggttt ttcaaaaccc acctcttcga | 1620 |
| ctgggtcacc agtgactcat tcggacgttg ccacctcctg gaactcccga ccgaccacaa | 1680 |
| aggtgtctac ggcagcctga cgactcgta tgcatatatg agaaacggct gggatgtcga | 1740 |

```
ggtcaccgcg gttggcaacc agttcaacgg agggtgcctg ctggtcgcaa tggtaccaga    1800
gcttcgttct atccaaaaga gggaactgta ccagctcaca cttttccctc accagttcat    1860
caacccacgc acgaacatga ctgcgcacat cacagtgccc tttgttggcg tcaaccgcta    1920
cgaccagtac aaggttcaca agccttggac ccttgtggtt atggttgtag ccctctgac    1980 cgtcaacact gaaggtgccc ctcagatcaa ggtgtatgcc aacattgccc caaccaacgt    2040
gcacgtcgcg ggtgagtttc cttccaagga gggaatattc cccgtggcct gtagcgacgg    2100
ctatggtggc ctggtgacca cggacccgaa gacggctgac cccgtttatg ggaaagtgtt    2160
caaccccccc cgcaaccagt tgccggggcg ttttaccaac ctccttgatg tggctgaggc    2220
atgcccgacg tttctgcact cgagggtga cgtaccgtac gtgaccacga aaacagactc    2280
ggacagggtg cttgctcagt ttgatatgtc tttggcagca aaacacatgt caaacacctt    2340
cctcgcaggt cttgcgcagt actacacaca gtacagtggc accatcaacc tgcacttcat    2400
gttcacagga cccactgacg cgaaggcgcg ttacatgatt gcctacgccc caccaggcat    2460
ggagccgccc aagacacctg aggcggccgc gcactgcatt catgctgaat gggacactgg    2520
gttgaactca aagtttactt tttccatccc ctacctctcg gccgccgatt acgcgtacac    2580
cgcgtctgac gtggccgaga ccacaaatgt gcagggatgg gtctgcttgt ttcaaattac    2640
acatggcaag gccgacggcg acgctctggt cgtactggct agtgctggta aagactttga    2700
gctaaggctg ccggtggacg cccgtgcgga aaccacttct gcgggcgagt cagcggatcc    2760
tgtcaccgcc actgttgaaa actacggtgg cgaaacacag atccagaggc gccaacacac    2820
ggacgtctcg ttcatcatgg acagatttgt gaaagtgaca ccgcaaaacc aaattaacat    2880
tttggacctc atgcagattc catcacacac tttggtggga cgctcctac gcgcgtccac    2940 ttactacttc tctgacttgg agatagcagt aaaacacgag ggagacctca cctgggttcc    3000
aaatggagcg cctgaaaagg cgttggacaa caccaccaac ccaactgctt accacaaggc    3060
accactcacc cggcttgccc tgccctacac cgcgccccac cgcgtgttgg caaccgtgta    3120
caacggtgag tgcaggtaca gcagaaatgc tgtgcccaac gtgagaggtg accttcaggt    3180
gttggctcaa aagtggcac ggacgctgcc tacctccttc aactacggtg ccatcaaagc    3240
gacccgggtc accgagttgc tttaccggat gaagagggcc gaaacatact gtccaaggcc    3300
cttgctggca atccacccaa ctgaagccag acacaaacag aaaattgtgg caccggtgaa    3360
acagttctga attttgacct tctcaagcta gccggagacg ttgagtccaa ccctgggccc    3420
ttcttcttct ccgacgttag gtcaaacttt tccaagctgg tagacacaat caaccagatg    3480
caggaagaca tgtccacaaa gcacggacct gactttaacc ggttggtgtc cgcttttgag    3540
gagttggcca ctgagtgaa agccatcagg accggtcttg acgaggccaa gccctggtac    3600
aagcttatca agctcctgag ccgcctgtcg tgcatggccg ctgtggcagc acggtcaaag    3660
gacccagtcc ttgtggccat catgctggct gacaccggtc tcgagattct ggacagcacc    3720
ttcgtcgtga agaagatctc cgactcgctc tccagtctct ccacgtgcc ggccccgtc    3780 ttcagtttcg gagccccgat tctgttagcc gggttggtca aggtcgcctc gagtttcttc    3840
cggtccacgc ccgaagacct tgagagagca gagaaacagc tcaaagcacg tgacatcaac    3900
gacattttcg ccattctcaa gaacggcgag tggctggtca aattgatcct tgccatccgc    3960
gactggatca aggcatggat agcctcagaa gaaaagtttg tcaccacgac agacttggta    4020
cctagcatcc ttgaaaaaca gcaggacctc aacgacccaa gcaagtacaa ggaagccaag    4080
```

```
gagtggctcg acaacgcgcg ccaagcgtgt ttgaagagcg ggaacgtcca cattgccaac    4140
ctgtgcaaag tggtcgcccc ggcacccagc aggtcgagac ccgagcccgt ggtcgtttgc    4200
ctccgtggca agtccggtca gggcaagagt ttccttgcaa acgtgctcgc acaagcaatc    4260
tctacccatt tcactggcag gaccgattca gtttggtact gcccgcctga ccctgaccac    4320
ttcgacggtt acaaccaaca gactgtcgtt gtgatggacg atttgggcca gaaccccgac    4380
ggcaaagact tcaagtactt cgcccaaatg gtttcaacaa cggggttcat cccgcccatg    4440
gcatcgcttg aggataaagg caaacccttc aacagtaagg tcatcatagc aaccaccaac    4500
ctgtactcgg gcttcacccc gaggactatg gtgtgccctg atgccctgaa ccggaggttt    4560
cactttgaca tcgacgtgag cgccaaggac gggtacaaaa ttaacaacaa attggacatc    4620
atcaaagcac ttgaagatac tcacaccaac ccagtggcaa tgtttcagta cgactgtgcc    4680
cttctcaacg gcatggctgt tgaaatgaag agaatgcaac aagatatgtt caagcctcaa    4740 ccacccttc agaacgtgta ccaactggtt caagaggtga ttgagcgggt ggagctccac    4800
gagaaggtgt cgagccaccc gattttcaaa cagatctcaa ttccttccca aaaatccgtg    4860
ttgtacttcc tcattgagaa aggacagcac gaggcagcaa ttgaattctt tgagggcatg    4920
gtgcacgact ccatcaagga ggagctccgg ccgctcatcc aacaaacctc atttgtgaaa    4980
cgcgctttta gcgcctgaa ggaaaacttt gagattgttg ccctatgtct gaccctcctg    5040
gccaacatag tgatcatgat ccgcgaaact cgcaagagac agaagatggt ggacgatgca    5100
gtgagtgagt acattgagag agcaaacatc accaccgacg acaagactct tgatgaggcg    5160
gaaaagaacc ctctggaaac cagcggtgcc agcaccgtcg gcttcagaga gagacctctc    5220
ccaggccaaa aggcgcgtaa tgacgagaac tccgagcccg cccagcctgc tgaagagcaa    5280
ccacaagctg aaggaccta cgctggcccg atggagagac cagttaaagt taaagtgaaa    5340
gcaaaagccc cggtcgttaa ggaaggacct tacgagggac cggtgaagaa gcctgttgct    5400
ttgaaagtga aagctaagaa cttgatcgtc actgagagtg gtgccccacc gaccgacttg    5460
caaaagttgg tcatgggcaa caccaagccc gttgagctca tccttgacgg gaagacggta    5520
gccatttgct gtgctactgg agttttcggc actgcttacc tcgtgcctcg tcatctttc    5580 gcagaaaagt acgacaagat catgttggac ggcagagcca tgacagatag tgactacaga    5640
gtgtttgagt ttgagattaa agtaaaagga caggacatgc tctcagacgc tgcgctcatg    5700
gtgctccacc gtgggaatcg cgtgagagac atcacgaaac actttcgtga cacagcaaga    5760
atgaagaaag gcaccccgt cgttggtgtg atcaacaacg ccgatgtcgg gagactgatt    5820
ttctctggtg aagcccttac ctacaaggac attgtagtgt gcatggatgg agacaccatg    5880
cctgggctct tgcctacaa agccgcaacc aaggctggtt attgcggagg agccgtcctc    5940
gctaaggacg gggctgacac gttcatcgtt ggcacccact ccgctggagg caatggcgtt    6000
ggatactgct cttgcgtttc caggtccatg cttctcaaga tgaaggcaca cgttgacccc    6060
gaaccacacc acgagggtt gattgttgac accagagatg tggaagagcg cgttcacgtg    6120
atgcgcaaaa ccaagcttgc acccaccgtt gcgtacggtg tgttccgtcc tgagttcggg    6180
cctgccgcct tgtccaacaa ggacccgcgc ctgaacgacg tgttgtcct cgacgaagtc    6240 atcttctcca aacacaaggg agacacaaag atgtctgagg aagacaaagc gctgttccgc    6300
cgctgtgctg ctgactacgc gtcacgcctg cacagcgtgt tgggtacggc aaatgcccca    6360
ctgagcatct acgaggcaat taaggcgtt gatggactcg acgcaatgga accagacacc    6420
gcacccggcc tcccctgggc actccagggg aagcgccgtg gcgcgctcat cgacttcgag    6480
```

```
aacggcactg ttggacccga agttgaggct gccttgaagc tcatggagaa aagagaatac    6540
aagtttgctt gccaaacctt cctgaaggac gagattcgcc cgatggagaa agtacgtgcc    6600
ggtaagactc gcattgtcga cgtcctacct gttgaacaca tcctctacac caggatgatg    6660
attggcagat tttgtgcaca aatgcactca acaacggac cccaaattgg ctcggcggtc    6720
ggttgtaacc ctgatgttga ttggcaaaga tttggcacac acttcgccca atacagaaac    6780
gtgtgggatg tggactattc ggccttcgat gctaaccact gcagtgacgc catgaacatc    6840
atgtttgagg aagtgtttcg cacagaattc gggttccacc caaacgctga gtggatcctg    6900
aagactctcg tgaacacgga acacgccat gagaacaaac gcatcactgt tgaaggcggg    6960
atgccatctg gttgttccgc aacaagcatc atcaacacaa ttttgaacaa catctacgtg    7020
ctctacgctt tgcgtagaca ctatgaggga gttgagctgg acacttacac catgatctct    7080
tacggagacg atatcgtggt ggcaagtgat tacgatttgg actttgaggc tctcaagccc    7140
cacttcaaat cccttggtca aaccatcact ccagctgaca aaagcgacaa aggttttgtt    7200
cttggtcact ccattactga tgtcactttc ctcaaaagac acttccacat ggattatgga    7260
actgggtttt acaaacctgt gatggcctca aagacccttg aggctatcct ctcctttgca    7320
cgccgtggga ccatacagga gaagttgatc tccgtggcag gactcgctgt tcactctgga    7380
ccagacgagt accggcgtct cttcgagccc tttcaaggcc tcttcgagat tccaagctac    7440
agatcacttt acctgcgttg ggtgaacgcc gtgtgcggcg acgcataatc cctcagagac    7500
tacattggca tactgtttct gaggcgcgcg acgccgtagg agtgaaaagc ctgaagggc    7560 ttttcccgct tcctattcca aaaaaaaaaa aaaaaa                              7597

<210> SEQ ID NO 26
<211> LENGTH: 7586
<212> TYPE: DNA
<213> ORGANISM: Artificial Sequence
<220> FEATURE:
<223> OTHER INFORMATION: Fusion Nucleotide Sequence containing C3
      Indaial strain of FMD (complete genome)

<400> SEQUENCE: 26
ttgaaagggg gcgctagggt ctcacccta gcatgccaac gacagtcccc gcgttgcact      60
ccacactcac gttgtgcgtg cgcggagctc gatggactat cgttcaccca cctacagctg    120
gactcacggc accgtgtggc cacttggctg gattgtgcgg acgaacaccg cttgcgcttc    180
tcgcgtgacc ggttagtact ctcaccacct tccgcccact tggttgttag cgctgtcttg    240
ggcactcctg ttgggggccg ttcgacgctc cgcgagtttc cccgcacggc aactacggtg    300
atggggccgt accgcgcggg ctgatcgcct ggtgtgcttc ggctgtcacc cgaagcctac    360
cttccacccc cccccccccc cccccccccc cccccctaa gttctaccgt                420 cgttcccgac gtaaagggat gtaaccacaa gcttactacc gcctttcccg gcgttaaagg    480
gatgtaacca caagacttac cttcacccgg aagtaaaacg gcaacttcac acagttttgc    540
ccgttttcat gagaaatggg acgtctgcgc acgaaacgcg ccgtcgcttg aggaggactt    600
gtacaaacac gatctaagca ggtttcccca actgacacaa accgtgcaat ttgaaactcc    660
gcctgggctt tccaggtcta gagggtgac actttgtact gtgtttgact ccacgttcga    720
tccactggcg agtgttagta acaacactgc tgcttcgtag cggagcatga cggccgtggg    780
accccccccc ttggtaacaa ggacccacgg ggccaaaagc cacgtccgaa tggacccgtc    840
atgtgtgcaa acccagcaca gtagctttgt tgtgaaactc actttaaagt gacattgata    900
```

-continued

```
ctggtactca agcactggtg acaggctaag gatgccttc aggtacccg aggtaacacg      960 tgacactcgg gatctgagaa ggggaccggg gcttctataa aagcgcccgg tttaaaaagc   1020
ttctatgtct gaataggtga ccggaggccg gcacctttct tttaattaca ctggacttat   1080
gaacacaact gattgtttta tcgctttggt acacgctatc agagagatca gagcattttt   1140
cctaccacga gccacaggaa tgggagccgg acaatccagc ccggcgactg gctcgcagaa   1200
ccaatctggc aacactggta gcataatcaa caactactac atgcaacagt accaaaattc   1260
catggacaca cagctgggtg acaatgctat tagtggtggc tccaacgagg gctccacaga   1320
tacaacttcc acccacacaa ccaacactca aaacaacgac tggttttcca aactcgccag   1380
ttctgccttt agcggtcttt tcggtgctct tcttgccgac aagaagaccg aggaaaccac   1440
actacttgaa gaccgcatcc tcaccacccg caacggccac acgacgtcga caactcagtc   1500
gagcgttggg gtcacatacg ggtacgcaac aactgaggat agcacgtcag ggcccaacac   1560
atccggcctt gagacacgtg ttcaccaggc agaacggttt ttcaagatga cactctttga   1620
atgggttccc tcccagagtt ttggacacat gcacaaggtc gttctgccct cagaaccgaa   1680
aggtgtctat gggggtctcg tcaagtcata cgcgtacatg cgcaatggct gggacgttga   1740
ggtgactgct gttggaaacc agttcaacgg cggttgtctc ctggtggcgc tcgttcctga   1800
aatgggtgac atcagtgaca gagagaagta ccaactgact ctctacccc accaattcat   1860 caacccacgc actaacatga cggcacacat caccgtgcct acgtgggtg tcaacagata   1920 cgaccaatac aaccaacaca gccctggac tcttgtcgtc atggtcgttg ctccacttac   1980
tgtgaacaca tcaggtgccc agcagatcaa ggtgtatgcc aacatagccc caaccaacgt   2040
tcacgttgct ggtgaacttc cctccaagga ggggatcttc cccgttgcgt gtgccgacgg   2100
ctatggcaac atggtgacaa ctgacccgaa gacagctgac cctgcctacg ggaaagtcta   2160
caatccaccc aggaccgccc tgccgggccg gttcacaaac tacctggatg ttgctgaggc   2220
ttgccccact ctcctgacgt tcgagaacgt gccttacgtt tcaacacgga ctgatggaca   2280
aaggctgttg gccaagttcg acgtgtcatt ggcagcgaaa cacatgtcaa acacttactt   2340
ggctggcttg gcccagtact acacacagta cgctgggaca atcaacctgc acttcatgtt   2400
cactgggcca accgacgcga aagctcggta catggtggca tacgtgcccc ctggcatgga   2460
agcaccagac aacccagagg aggctgccca ctgcatacac gcagagtggg acactggttt   2520
gaactctaag ttcacatttt caatcccgta catctcggcc gctgactacg catacaccgc   2580
gtccagcgag gctgaaacaa caagcgtaca gggatgggtt tgtgtgtacc agatcactca   2640
cggcaaggca gacgctgacg cgctcgtcgt ctccgcttcg gcggggaaag actttgagct   2700
ccggctacct gtgacgcta gacagcaaac tacgaccact ggcgaatctg ccgaccccgt   2760
caccactacc gttgagaact acggaggaga aacacaaact caacgtcgcc accacactga   2820
cgttgccttc gttcttgacc ggtttgtgaa ggtccaggtg tcgggcaacc aacacacact   2880
ggacgttatg caggtacaca aggacagtat tgtgggtgca ctcctacgcg cagccacata   2940
ctacttctct gacttggaaa tagcagtgac tcacactggg aagctcacat gggtgcccaa   3000
cggcgcccca gtttctgcac ttgacaacac aaccaacccc actgcctacc acaaggggcc   3060
gctgactcgg ctggctctcc catacaccgc accacaccgc gtgctggcca cggcgtacac   3120
cggtacaacg gcctacacta ccggtgtacg caggggagac ctagcccact tggcggcggc   3180
gcacgctcgg cacctgccga cgtcgttcaa ctttggtgca gttaaagcag agacaatcac   3240
```

```
agagctgctt gtgcgcatga agcgtgctga actctactgc cccagaccgg tccttccggt    3300
ccaaccagcg ggcgataggc acaaacaacc gctcattgcg ccagcgaaac agcttctgaa    3360
ttttgacctg cttaagctag ccggagacgt tgagtccaac cctgggccct tcttcttctc    3420
cgacgttagg tcaaacttttt ccaagctggt agacacaatc aaccagatgc aggaagacat    3480
gtccacaaag cacggacctg actttaaccg gttggtgtcc gcttttgagg agttggccac    3540
tggagtgaaa gccatcagga ccggtcttga cgaggccaag ccctggtaca agcttatcaa    3600
gctcctgagc cgcctgtcgt gcatggccgc tgtggcagca cggtcaaagg acccagtcct    3660
tgtggccatc atgctggctg acaccggtct cgagattctg acagcacct tcgtcgtgaa    3720
gaagatctcc gactcgctct ccagtctctt ccacgtgccg gcccccgtct tcagtttcgg    3780
agccccgatt ctgttagccg ggttggtcaa ggtcgcctcg agtttcttcc ggtccacgcc    3840
cgaagacctt gagagagcag agaaacagct caaagcacgt gacatcaacg acattttcgc    3900
cattctcaag aacggcgagt ggctggtcaa attgatcctt gccatccgcg actggatcaa    3960
ggcatggata gcctcagaag aaaagtttgt caccacgaca gacttggtac ctagcatcct    4020
tgaaaaacag caggacctca acgacccaag caagtacaag gaagccaagg agtggctcga    4080
caacgcgcgc aagcgtgtt tgaagagcgg gaacgtccac attgccaacc tgtgcaaagt    4140
ggtcgccccg gcacccagca ggtcgagacc cgagcccgtg gtcgtttgcc tccgtggcaa    4200
gtccggtcag ggcaagagtt ccttgcaaa cgtgctcgca caagcaatct ctacccattt    4260
cactggcagg accgattcag tttggtactg cccgcctgac cctgaccact tcgacggtta    4320
caaccaacag actgtcgttg tgatggacga tttgggccag aaccccgacg gcaaagactt    4380
caagtacttc gcccaaatgg tttcaacaac ggggttcatc ccgcccatgg catcgcttga    4440
ggataaaggc aaaccccttca acagtaaggt catcatagca accaccaacc tgtactcggg    4500
cttcacccg aggactatgg tgtgccctga tgccctgaac cggaggtttc actttgacat    4560
cgacgtgagc gccaaggacg ggtacaaaat taacaacaaa ttggacatca tcaaagcact    4620
tgaagatact cacaccaacc cagtggcaat gtttcagtac gactgtgccc ttctcaacgg    4680
catggctgtt gaaatgaaga gaatgcaaca agatatgttc aagcctcaac cacccttca    4740
gaacgtgtac caactggttc aagaggtgat tgagcgggtg gagctccacg agaaggtgtc    4800
gagccacccg attttcaaac agatctcaat tccttcccaa aaatccgtgt tgtacttcct    4860
cattgagaaa ggacagcacg aggcagcaat tgaattcttt gagggcatgg tgcacgactc    4920
catcaaggag gagctccggc cgctcatcca acaaaacctca tttgtgaaac gcgcttttaa    4980
gcgcctgaag gaaaactttg agattgttgc cctatgtctg accctcctgg ccaacatagt    5040
gatcatgatc cgcgaaactc gcaagagaca aagatggtg gacgatgcag tgagtgagta    5100
cattgagaga gcaaacatca ccaccgacga caagactctt gatgaggcgg aaaagaaccc    5160
tctggaaacc agcggtgcca gcaccgtcgg cttcagagag agacctctcc caggccaaaa    5220
ggcgcgtaat gacgagaact ccgagcccgc ccagcctgct gaagagcaac acaagctga    5280
aggaccctac gctggcccga tggagagacc agttaaagtt aaagtgaaag caaaagcccc    5340
ggtcgttaag gaaggacctt acgagggacc ggtgaagaag cctgttgctt tgaaagtgaa    5400
agctaagaac ttgatcgtca ctgagagtgg tgccccaccg accgacttgc aaaagttggt    5460
catgggcaac accaagcccg ttgagctcat ccttgacggg aagacggtag ccatttgctg    5520
tgctactgga gttttcggca ctgcttacct cgtgcctcgt catcttttcg cagaaaagta    5580
cgacaagatc atgttggacg gcagagccat gacagatagt gactacagag tgtttgagtt    5640
```

```
tgagattaaa gtaaaaggac aggacatgct ctcagacgct gcgctcatgg tgctccaccg    5700
tgggaatcgc gtgagagaca tcacgaaaca ctttcgtgac acagcaagaa tgaagaaagg    5760 caccccgtc gttggtgtga tcaacaacgc cgatgtcggg agactgattt tctctggtga     5820
agcccttacc tacaaggaca ttgtagtgtg catggatgga gacaccatgc ctgggctctt    5880
tgcctacaaa gccgcaacca aggctggtta ttgcggagga gccgtcctcg ctaaggacgg    5940
ggctgacacg ttcatcgttg cacccactc cgctggaggc aatggcgttg gatactgctc     6000
ttgcgtttcc aggtccatgc ttctcaagat gaaggcacac gttgaccccg aaccacacca    6060 cgagggggttg attgttgaca ccagagatgt ggaagagcgc gttcacgtga tgcgcaaaac   6120
caagcttgca cccaccgttg cgtacggtgt gttccgtcct gagttcgggc ctgccgcctt    6180
gtccaacaag gacccgcgcc tgaacgacgg tgttgtcctc gacgaagtca tcttctccaa    6240
acacaaggga gacacaaaga tgtctgagga agacaaagcg ctgttccgcc gctgtgctgc    6300
tgactacgcg tcacgcctgc acagcgtgtt gggtacggca aatgcccacc tgagcatcta    6360
cgaggcaatt aaaggcgttg atggactcga cgcaatggaa ccagacaccg cacccggcct    6420
cccctgggca ctccagggga agcgccgtgg cgcgctcatc gacttcgaga acggcactgt    6480 tggaccccgaa gttgaggctg ccttgaagct catggagaaa agagaataca gtttgcttg    6540 ccaaaccttc ctgaaggacg agattcgccc gatggagaaa gtacgtgccg gtaagactcg    6600
cattgtcgac gtcctacctg ttgaacacat cctctacacc aggatgatga ttggcagatt    6660
ttgtgcacaa atgcactcaa acaacggacc ccaaattggc tcggcggtcg gttgtaaccc    6720
tgatgttgat tggcaaagat ttggcacaca cttcgcccaa tacagaaacg tgtgggatgt    6780
ggactattcg gccttcgatg ctaaccactg cagtgacgcc atgaacatca tgtttgagga    6840
agtgtttcgc acagaattcg ggttccaccc aaacgctgag tggatcctga agactctcgt    6900
gaacacggaa cacgcctatg agaacaaacg catcactgtt gaaggcggga tgccatctgg    6960
ttgttccgca acaagcatca tcaacacaat tttgaacaac atctacgtgc tctacgcttt    7020
gcgtagacac tatgagggag ttgagctgga cacttacacc atgatctctt acggagacga    7080
tatcgtggtg gcaagtgatt acgatttgga cttt gaggct ctcaagcccc acttcaaatc   7140
ccttggtcaa accatcactc cagctgacaa aagcgacaaa ggttttgttc ttggtcactc    7200
cattactgat gtcactttcc tcaaaagaca cttcccacatg gattatgaa ctgggttta     7260 caaacctgtg atggcctcaa agacccttga ggctatcctc tcctttgcac gccgtgggac    7320
catacaggag aagttgatct ccgtggcagg actcgctgtt cactctggac cagacgagta    7380
ccggcgtctc ttcgagccct ttcaaggcct cttcgagatt ccaagctaca gatcacttta    7440
cctgcgttgg gtgaacgccg tgtgcggcga cgcataatcc ctcagagact acattggcat    7500
actgtttctg aggcgcgcga cgccgtagga gtgaaaagcc tgaaagggct tttcccgctt    7560
cctattccaa aaaaaaaaaa aaaaaa                                        7586
```

<210> SEQ ID NO 27
<211> LENGTH: 2076
<212> TYPE: DNA
<213> ORGANISM: Artificial Sequence
<220> FEATURE:
<223> OTHER INFORMATION: Fusion Nucleotide Sequence containing capsid and 2A partial sequence of C3 Indaial strain of FMD

<400> SEQUENCE: 27

```
ggggccggcc aatccagccc agctactggc tcgcagaacc aatctggtaa cacaggtagc    60
```

```
ataatcaaca actactacat gcaacagtac caaaactcca tggacacaca gcttggtgac      120
aatgccatca gtggaggctc taacgagggc tccacggaca caacttcaac tcacacaacc      180
aacacccaaa acaatgactg gttttcaaga ctcgccggtt cggccttctc cggtttgttt      240
ggggccttgc ttgccgacaa gaagacggag gagacgacac tccttgagga ccgcattctc      300
accactcgca atgggcacac cacctccacg acccagtcca gcgtaggcgt tacatacggg      360
tactccacaa cagaggacca cgttgctgga cccaacacat caggtttgga gacacgagtg      420
gtacaggcag agagattcta caaaaagttt tgtttgatt ggacaacgga caagccttt       480 ggacacctgc acaaactgga gttgcccacc gaccaccacg tgttttcgg acacttggtg      540 gactcatacg cctacatgag gaacggttgg gacgttgagg tgtctgctgt tggcaaccag      600
ttcaacggcg gatgcctcct agtggccatg gtacccgaat ggaaagagtt tgaaacgcgg      660
gagaagtacc agctcacgct ttttcccgcac cagttcatta gccccagaac caacatgacc      720
gcccacatca cggttcctta ccttggtgtg aatagatatg atcagtacaa aaaacacaaa      780
ccctggacac tggttgtcat ggtcgtgtcc ccgctcacgg tcaacgccac gagcgcggca      840
cagatcaagg tctatgccaa catcgctccg acctacgttc atgtggccgg cgagctcccc      900
tcgaaagagg ggatcttccc tgtcgcgtgc gcggacggtt acggaggact ggtgacaacg      960
gacccgaaaa cagctgaccc cgcctacggc aaggtgtaca atccgccccg gactaactac     1020
cccgggcgtt tcactaactt gttggacgtg gctgaggcat gtcccacctt tctgtgttt      1080 gacgacggga aaccgtacgt taccacacag acaggtgagt ctcgtcttct ggccaagttc     1140
gacctttccc ttgccgcgaa gcacatgtct aacacatact tggcaggaat tgcccagtac     1200
tacacacagt actcaggcac catcaatttg catttcatgt tcacaggttc aactgattca     1260
aaagcccgct acatggtggc ttacatcccg cctggggtgg aaacaccacc ggacacacct     1320
gagagggcag cccactgcat ccatgctgag tgggacacag gctgaattc caaattcaca     1380 ttctcaatcc cgtacgtgtc tgccgcggat tacgcctaca cggcgtctga tgaggcagag     1440
acaacaaacg tacagggatg ggtctgcgtt taccagatca cacacgggaa ggctgacaac     1500
gacactctgg tcgtgtcggt tagcgccggc aaggacttcg agttgcgcct ccccattgac     1560
ccccgaccgc agaccaccgc tactggggaa tcagcagacc ctgtcaccac cactgtagag     1620
aactacggcg gtgagacaca agttcagaga cgccaccaca ccgacgttgg cttcatcatg     1680
gacagatttg tgaaaataaa cagcccaaaa tccacccatg ttattgacct catgcaaacc     1740
caccaacacg gtctagtggg tgcgctgctg cgtgcggcga cctactactt ctcagatctg     1800
gaaattgttg tgcggcatga cggcaaccta acttgggtgc ccaatggtgc tcccgtgtca     1860
gccttgtcca acaccagcaa ccccaccgcc tacaacaagg caccgttcac gagacttgcc     1920
ctcccctaca ccgcgccaca ccgcgtgttg gcgactgtgt acaacgggac gagcaagtac     1980
actgtgagtg ggtcaagcag acgaggcgac ttgggttccc tcgcggcacg agtcgtgaag     2040
gcacttcctg cttctttcaa ctacggtgca atcaag                                2076
```

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28

```
gacaaaggtt ttgttcttgg tca                                              23

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
tgcgagtcct gccacgga                                                    18

<210> SEQ ID NO 30
<211> LENGTH: 20
<212> TYPE: DNA
<213> ORGANISM: Artificial Sequence
<220> FEATURE:
<223> OTHER INFORMATION: Probe

<400> SEQUENCE: 30
tcctttgcac gccgtgggac                                                  20
```